US011510935B2

(12) United States Patent
Kim et al.

(10) Patent No.: US 11,510,935 B2
(45) Date of Patent: Nov. 29, 2022

(54) GUIDE RNA COMPLEMENTARY TO KRAS GENE, AND USE THEREOF

(71) Applicant: Industry-Academic Cooperation Foundation, Yonsei University, Seoul (KR)

(72) Inventors: Hyong Bum Kim, Seoul (KR); Won Joo Kim, Seoul (KR); Han Sang Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 460 days.

(21) Appl. No.: 16/341,585

(22) PCT Filed: Oct. 16, 2017

(86) PCT No.: PCT/KR2017/011391
§ 371 (c)(1),
(2) Date: Apr. 12, 2019

(87) PCT Pub. No.: WO2018/070850
PCT Pub. Date: Apr. 19, 2018

(65) Prior Publication Data

US 2019/0255094 A1 Aug. 22, 2019

(30) Foreign Application Priority Data

Oct. 14, 2016 (KR) ........................ 10-2016-0133777
Oct. 13, 2017 (KR) ........................ 10-2017-0133485

(51) Int. Cl.
*A61K 31/7105* (2006.01)
*A61P 35/00* (2006.01)
*C12N 15/113* (2010.01)
*C12N 15/86* (2006.01)

(52) U.S. Cl.
CPC .......... *A61K 31/7105* (2013.01); *A61P 35/00* (2018.01); *C12N 15/113* (2013.01); *C12N 15/1135* (2013.01); *C12N 15/86* (2013.01); *C12N 2310/20* (2017.05); *C12N 2750/14141* (2013.01)

(58) Field of Classification Search
CPC .. C12N 9/22; C12N 2310/20; C12N 2800/80; C12Q 1/6827; C12Q 2521/301
USPC ..................... 435/6.1, 91.1, 91.31, 455, 458; 514/44 A, 44 R; 536/23.1, 24.5
See application file for complete search history.

(56) References Cited

U.S. PATENT DOCUMENTS 5,847,095 A * 12/1998 Bos ...................... C12Q 1/6886 536/23.1
9,523,119 B2 * 12/2016 Yamane ............... C12Q 1/6858
9,687,500 B2 * 6/2017 Shemi .................. A61K 9/5031
10,053,737 B2 * 8/2018 Chang ................. C12Q 1/6886
2016/0017301 A1 1/2016 Khalili et al.
2019/0330603 A1 * 10/2019 Ahlfors .................. C12N 15/11
2021/0147933 A1 * 5/2021 Chiang ................ C12Q 1/6876
2022/0073923 A1 * 3/2022 Pecot ...................... A61P 35/00

FOREIGN PATENT DOCUMENTS

EP 3346003 A1 7/2018
WO WO-2013157010 A1 * 10/2013 ............. A61P 35/04
WO 2015/179540 A1 11/2015
WO 2016/095931 A2 6/2016
WO 2017/053762 A1 3/2017
WO WO-2017218512 A1 * 12/2017 .............. C12N 9/22

OTHER PUBLICATIONS

Han et al, J. Molec. Med., vol. 98, pp. 615-632. (Year: 2020).*
Tan, C. et al., KRAS Mutation Testing in Metastatic Colorectal Cancer, World Journal of Gastroenterology, 18(37): 5171-5180, Oct. 7, 2012.
Roszkowski, K. et al., Impact of Specific KRAS Mutation in Exon 2 on Clinical Outcome of Chemotherapy- and Radiotherapy—ti eated Colorectal Adenocarcinoma Patients, Molecular Diagnosis & Therapy, 18: 559-566, 2014.
Neumann, J. et al., Frequency and type of KRAS mutations in routine diagnostic analysis of metastatic colorectal cancer, Pathology—Research and Practice, 205: 858-862, 2009.

* cited by examiner

*Primary Examiner* — Jane J Zara
(74) *Attorney, Agent, or Firm* — Burris Law, PLLC

(57) ABSTRACT

According to an aspect, provided are: a guide RNA; a vector comprising the same; a composition for removing a nucleic acid sequence encoding a KRAS polypeptide in the genome of a cell, containing the same; a composition for preventing or treating cancer, containing the same; and a method using the same. The present invention enables the mutation of a nucleic acid sequence encoding a KRAS polypeptide in the genome of a cell or a subject and, particularly, can be usable, as personalized or precision medical care, in the prevention or treatment of cancer.

15 Claims, 17 Drawing Sheets

Specification includes a Sequence Listing.

LENTI_gRNA-PURO

LENTI_gRNA-DOXY-INDUCIBLE_GFP

LENTI_SpCas9-Blast $P_{CMV}$
mRFP
STOP
eGFP
OUT OF FRAME (+1)
eGFP
OUT OF FRAME (+2)
mRFP+eGFP−
CRISPR Cas9–INDUCED DOUBLE–STRAND BREAK
Cas9
sgRNA
OUT OF FRAME
NONHOMOLOGOUS END JOINING–MEDIATED FRAME–SHIFT MUTATION
INDEL FORMATION
IN FRAME
mRFP+eGFP+

FIG. 2E

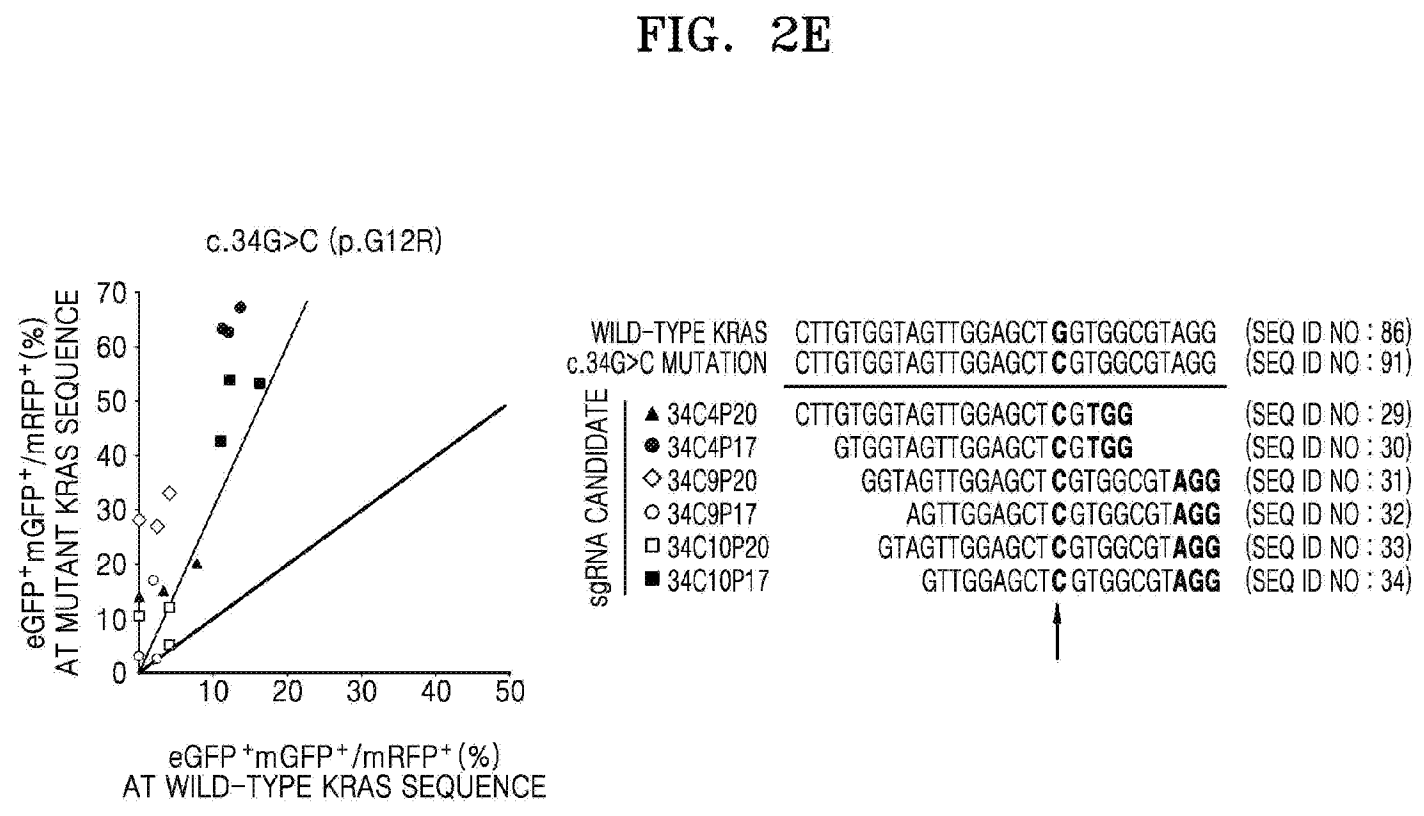

| | | |
|---|---|---|
| WILD-TYPE KRAS | CTTGTGGTAGTTGGAGCT**G**GTGGCGTAGG | (SEQ ID NO : 86) |
| c.34G>C MUTATION | CTTGTGGTAGTTGGAGCT**C**GTGGCGTAGG | (SEQ ID NO : 91) |
| sgRNA CANDIDATE ▲ 34C4P20 | CTTGTGGTAGTTGGAGCT**C**G**TGG** | (SEQ ID NO : 29) |
| ● 34C4P17 | GTGGTAGTTGGAGCT**C**G**TGG** | (SEQ ID NO : 30) |
| ◇ 34C9P20 | GGTAGTTGGAGCT**C**GTGGCGT**AGG** | (SEQ ID NO : 31) |
| ○ 34C9P17 | AGTTGGAGCT**C**GTGGCGT**AGG** | (SEQ ID NO : 32) |
| □ 34C10P20 | GTAGTTGGAGCT**C**GTGGCGT**AGG** | (SEQ ID NO : 33) |
| ■ 34C10P17 | GTTGGAGCT**C**GTGGCGT**AGG** | (SEQ ID NO : 34) |

SEQUENCE LISTING

```
<160> NUMBER OF SEQ ID NOS: 92

<210> SEQ ID NO 1
<211> LENGTH: 23
<212> TYPE: DNA
<213> ORGANISM: Artificial Sequence
<220> FEATURE:
<223> OTHER INFORMATION: Target KRAS sequence targeted by guide RNA
      35T3P20

<400> SEQUENCE: 1

cttgtggtag ttggagctgt tgg                                          23


<210> SEQ ID NO 2
<211> LENGTH: 20
<212> TYPE: DNA
<213> ORGANISM: Artificial Sequence
<220> FEATURE:
<223> OTHER INFORMATION: Target KRAS sequence targeted by guide RNA
      35T3P17

<400> SEQUENCE: 2

gtggtagttg gagctgttgg                                              20


<210> SEQ ID NO 3
<211> LENGTH: 23
<212> TYPE: DNA
<213> ORGANISM: Artificial Sequence
<220> FEATURE:
<223> OTHER INFORMATION: Target KRAS sequence targeted by guide RNA
      35T8P20

<400> SEQUENCE: 3

ggtagttgga gctgttggcg tag                                          23


<210> SEQ ID NO 4
<211> LENGTH: 20
<212> TYPE: DNA
<213> ORGANISM: Artificial Sequence
<220> FEATURE:
<223> OTHER INFORMATION: Target KRAS sequence targeted by guide RNA
      35T8P17

<400> SEQUENCE: 4

agttggagct gttggcgtag                                              20


<210> SEQ ID NO 5
<211> LENGTH: 23
<212> TYPE: DNA
<213> ORGANISM: Artificial Sequence
<220> FEATURE:
<223> OTHER INFORMATION: Target KRAS sequence targeted by guide RNA
      35T9P20

<400> SEQUENCE: 5

gtagttggag ctgttggcgt agg                                          23
```

<210> SEQ ID NO 6
<211> LENGTH: 20
<212> TYPE: DNA
<213> ORGANISM: Artificial Sequence
<220> FEATURE:
<223> OTHER INFORMATION: Target KRAS sequence targeted by guide RNA 35T9P17

<400> SEQUENCE: 6
gttggagctg ttggcgtagg 20

<210> SEQ ID NO 7
<211> LENGTH: 23
<212> TYPE: DNA
<213> ORGANISM: Artificial Sequence
<220> FEATURE:
<223> OTHER INFORMATION: Target KRAS sequence targeted by guide RNA 35T3M20

<400> SEQUENCE: 7
ctgttggcgt aggcaagagt gcc 23

<210> SEQ ID NO 8
<211> LENGTH: 20
<212> TYPE: DNA
<213> ORGANISM: Artificial Sequence
<220> FEATURE:
<223> OTHER INFORMATION: Target KRAS sequence targeted by guide RNA 35T3M17

<400> SEQUENCE: 8
ctgttggcgt aggcaagagt 20

<210> SEQ ID NO 9
<211> LENGTH: 23
<212> TYPE: DNA
<213> ORGANISM: Artificial Sequence
<220> FEATURE:
<223> OTHER INFORMATION: Target KRAS sequence targeted by guide RNA 35A3P20

<400> SEQUENCE: 9
cttgtggtag ttggagctga tgg 23

<210> SEQ ID NO 10
<211> LENGTH: 20
<212> TYPE: DNA
<213> ORGANISM: Artificial Sequence
<220> FEATURE:
<223> OTHER INFORMATION: Target KRAS sequence targeted by guide RNA 35A3P17

<400> SEQUENCE: 10
gtggtagttg gagctgatgg 20

<210> SEQ ID NO 11
<211> LENGTH: 23
<212> TYPE: DNA
<213> ORGANISM: Artificial Sequence
<220> FEATURE:
<223> OTHER INFORMATION: Target KRAS sequence targeted by guide RNA 35A8P20

<400> SEQUENCE: 11
ggtagttgga gctgatggcg tag 23

<210> SEQ ID NO 12

<211> LENGTH: 20
<212> TYPE: DNA
<213> ORGANISM: Artificial Sequence
<220> FEATURE:
<223> OTHER INFORMATION: Target KRAS sequence targeted by guide RNA 35A8P17

<400> SEQUENCE: 12
agttggagct gatggcgtag 20

<210> SEQ ID NO 13
<211> LENGTH: 23
<212> TYPE: DNA
<213> ORGANISM: Artificial Sequence
<220> FEATURE:
<223> OTHER INFORMATION: Target KRAS sequence targeted by guide RNA 35A9P20

<400> SEQUENCE: 13
gtagttggag ctgatggcgt agg 23

<210> SEQ ID NO 14
<211> LENGTH: 20
<212> TYPE: DNA
<213> ORGANISM: Artificial Sequence
<220> FEATURE:
<223> OTHER INFORMATION: Target KRAS sequence targeted by guide RNA 35A9P17

<400> SEQUENCE: 14
gttggagctg atggcgtagg 20

<210> SEQ ID NO 15
<211> LENGTH: 23
<212> TYPE: DNA
<213> ORGANISM: Artificial Sequence
<220> FEATURE:
<223> OTHER INFORMATION: Target KRAS sequence targeted by guide RNA 35A3M20

<400> SEQUENCE: 15
ctgatggcgt aggcaagagt gcc 23

<210> SEQ ID NO 16
<211> LENGTH: 20
<212> TYPE: DNA
<213> ORGANISM: Artificial Sequence
<220> FEATURE:
<223> OTHER INFORMATION: Target KRAS sequence targeted by guide RNA 35A3M17

<400> SEQUENCE: 16
ctgatggcgt aggcaagagt 20

<210> SEQ ID NO 17
<211> LENGTH: 23
<212> TYPE: DNA
<213> ORGANISM: Artificial Sequence
<220> FEATURE:
<223> OTHER INFORMATION: Target KRAS sequence targeted by guide RNA 38A6P20

<400> SEQUENCE: 17
gtagttggag ctggtgacgt agg 23

<210> SEQ ID NO 18
<211> LENGTH: 20

<212> TYPE: DNA
<213> ORGANISM: Artificial Sequence
<220> FEATURE:
<223> OTHER INFORMATION: Target KRAS sequence targeted by guide RNA 38A6P17

<400> SEQUENCE: 18
gttggagctg gtgacgtagg 20

<210> SEQ ID NO 19
<211> LENGTH: 23
<212> TYPE: DNA
<213> ORGANISM: Artificial Sequence
<220> FEATURE:
<223> OTHER INFORMATION: Target KRAS sequence targeted by guide RNA 38A5P20

<400> SEQUENCE: 19
ggtagttgga gctggtgacg tag 23

<210> SEQ ID NO 20
<211> LENGTH: 20
<212> TYPE: DNA
<213> ORGANISM: Artificial Sequence
<220> FEATURE:
<223> OTHER INFORMATION: Target KRAS sequence targeted by guide RNA 38A5P17

<400> SEQUENCE: 20
agttggagct ggtgacgtag 20

<210> SEQ ID NO 21
<211> LENGTH: 23
<212> TYPE: DNA
<213> ORGANISM: Artificial Sequence
<220> FEATURE:
<223> OTHER INFORMATION: Target KRAS sequence targeted by guide RNA 38A6M20

<400> SEQUENCE: 21
ctggtgacgt aggcaagagt gcc 23

<210> SEQ ID NO 22
<211> LENGTH: 20
<212> TYPE: DNA
<213> ORGANISM: Artificial Sequence
<220> FEATURE:
<223> OTHER INFORMATION: Target KRAS sequence targeted by guide RNA 38A6M17

<400> SEQUENCE: 22
ctggtgacgt aggcaagagt 20

<210> SEQ ID NO 23
<211> LENGTH: 23
<212> TYPE: DNA
<213> ORGANISM: Artificial Sequence
<220> FEATURE:
<223> OTHER INFORMATION: Target KRAS sequence targeted by guide RNA 34T4P20

<400> SEQUENCE: 23
cttgtggtag ttggagcttg tgg 23

<210> SEQ ID NO 24
<211> LENGTH: 20
<212> TYPE: DNA

<213> ORGANISM: Artificial Sequence
<220> FEATURE:
<223> OTHER INFORMATION: Target KRAS sequence targeted by guide RNA 34T4P17

<400> SEQUENCE: 24
gtggtagttg gagcttgtgg 20

<210> SEQ ID NO 25
<211> LENGTH: 23
<212> TYPE: DNA
<213> ORGANISM: Artificial Sequence
<220> FEATURE:
<223> OTHER INFORMATION: Target KRAS sequence targeted by guide RNA 34T9P20

<400> SEQUENCE: 25
ggtagttgga gcttgtggcg tag 23

<210> SEQ ID NO 26
<211> LENGTH: 20
<212> TYPE: DNA
<213> ORGANISM: Artificial Sequence
<220> FEATURE:
<223> OTHER INFORMATION: Target KRAS sequence targeted by guide RNA 34T9P17

<400> SEQUENCE: 26
agttggagct tgtggcgtag 20

<210> SEQ ID NO 27
<211> LENGTH: 23
<212> TYPE: DNA
<213> ORGANISM: Artificial Sequence
<220> FEATURE:
<223> OTHER INFORMATION: Target KRAS sequence targeted by guide RNA 34T10P20

<400> SEQUENCE: 27
gtagttggag cttgtggcgt agg 23

<210> SEQ ID NO 28
<211> LENGTH: 20
<212> TYPE: DNA
<213> ORGANISM: Artificial Sequence
<220> FEATURE:
<223> OTHER INFORMATION: Target KRAS sequence targeted by guide RNA 34T10P17

<400> SEQUENCE: 28
gttggagctt gtggcgtagg 20

<210> SEQ ID NO 29
<211> LENGTH: 23
<212> TYPE: DNA
<213> ORGANISM: Artificial Sequence
<220> FEATURE:
<223> OTHER INFORMATION: Target KRAS sequence targeted by guide RNA 34C4P20

<400> SEQUENCE: 29
cttgtggtag ttggagctcg tgg 23

<210> SEQ ID NO 30
<211> LENGTH: 20
<212> TYPE: DNA
<213> ORGANISM: Artificial Sequence
<220> FEATURE:
<223> OTHER INFORMATION: Target KRAS sequence targeted by guide RNA 34C4P17

<400> SEQUENCE: 30
gtggtagttg gagctcgtgg 20

<210> SEQ ID NO 31
<211> LENGTH: 23
<212> TYPE: DNA
<213> ORGANISM: Artificial Sequence
<220> FEATURE:
<223> OTHER INFORMATION: Target KRAS sequence targeted by guide RNA 34C9P20

<400> SEQUENCE: 31
ggtagttgga gctcgtggcg tag 23

<210> SEQ ID NO 32
<211> LENGTH: 20
<212> TYPE: DNA
<213> ORGANISM: Artificial Sequence
<220> FEATURE:
<223> OTHER INFORMATION: Target KRAS sequence targeted by guide RNA 34C9P17

<400> SEQUENCE: 32
agttggagct cgtggcgtag 20

<210> SEQ ID NO 33
<211> LENGTH: 23
<212> TYPE: DNA
<213> ORGANISM: Artificial Sequence
<220> FEATURE:
<223> OTHER INFORMATION: Target KRAS sequence targeted by guide RNA 34C10P20

<400> SEQUENCE: 33
gtagttggag ctcgtggcgt agg 23

<210> SEQ ID NO 34
<211> LENGTH: 20
<212> TYPE: DNA
<213> ORGANISM: Artificial Sequence
<220> FEATURE:
<223> OTHER INFORMATION: Target KRAS sequence targeted by guide RNA 34C10P17

<400> SEQUENCE: 34
gttggagctc gtggcgtagg 20

<210> SEQ ID NO 35
<211> LENGTH: 23
<212> TYPE: DNA
<213> ORGANISM: Artificial Sequence
<220> FEATURE:
<223> OTHER INFORMATION: Target KRAS sequence targeted by guide RNA 35C3M20

<400> SEQUENCE: 35
ctgctggcgt aggcaagagt gcc 23

<210> SEQ ID NO 36
<211> LENGTH: 20
<212> TYPE: DNA
<213> ORGANISM: Artificial Sequence
<220> FEATURE:

<223> OTHER INFORMATION: Target KRAS sequence targeted by guide RNA 35C3M17

<400> SEQUENCE: 36
ctgctggcgt aggcaagagt 20

<210> SEQ ID NO 37
<211> LENGTH: 23
<212> TYPE: DNA
<213> ORGANISM: Artificial Sequence
<220> FEATURE:
<223> OTHER INFORMATION: Target KRAS sequence targeted by guide RNA 35C3P20

<400> SEQUENCE: 37
cttgtggtag ttggagctgc tgg 23

<210> SEQ ID NO 38
<211> LENGTH: 20
<212> TYPE: DNA
<213> ORGANISM: Artificial Sequence
<220> FEATURE:
<223> OTHER INFORMATION: Target KRAS sequence targeted by guide RNA 35C3P17

<400> SEQUENCE: 38
gtggtagttg gagctgctgg 20

<210> SEQ ID NO 39
<211> LENGTH: 23
<212> TYPE: DNA
<213> ORGANISM: Artificial Sequence
<220> FEATURE:
<223> OTHER INFORMATION: Target KRAS sequence targeted by guide RNA 35C8P20

<400> SEQUENCE: 39
ggtagttgga gctgctggcg tag 23

<210> SEQ ID NO 40
<211> LENGTH: 20
<212> TYPE: DNA
<213> ORGANISM: Artificial Sequence
<220> FEATURE:
<223> OTHER INFORMATION: Target KRAS sequence targeted by guide RNA 35C8P17

<400> SEQUENCE: 40
agttggagct gctggcgtag 20

<210> SEQ ID NO 41
<211> LENGTH: 23
<212> TYPE: DNA
<213> ORGANISM: Artificial Sequence
<220> FEATURE:
<223> OTHER INFORMATION: Target KRAS sequence targeted by guide RNA 35C9P20

<400> SEQUENCE: 41
gtagttggag ctgctggcgt agg 23

<210> SEQ ID NO 42
<211> LENGTH: 20
<212> TYPE: DNA
<213> ORGANISM: Artificial Sequence
<220> FEATURE:
<223> OTHER INFORMATION: Target KRAS sequence targeted by guide RNA

35C9P17

<400> SEQUENCE: 42
gttggagctg ctggcgtagg 20

<210> SEQ ID NO 43
<211> LENGTH: 20
<212> TYPE: DNA
<213> ORGANISM: Artificial Sequence
<220> FEATURE:
<223> OTHER INFORMATION: guide RNA 35T3P20

<400> SEQUENCE: 43
cttgtggtag ttggagctgt 20

<210> SEQ ID NO 44
<211> LENGTH: 17
<212> TYPE: DNA
<213> ORGANISM: Artificial Sequence
<220> FEATURE:
<223> OTHER INFORMATION: guide RNA 35T3P17

<400> SEQUENCE: 44
gtggtagttg gagctgt 17

<210> SEQ ID NO 45
<211> LENGTH: 20
<212> TYPE: DNA
<213> ORGANISM: Artificial Sequence
<220> FEATURE:
<223> OTHER INFORMATION: guide RNA 35T8P20

<400> SEQUENCE: 45
ggtagttgga gctgttggcg 20

<210> SEQ ID NO 46
<211> LENGTH: 17
<212> TYPE: DNA
<213> ORGANISM: Artificial Sequence
<220> FEATURE:
<223> OTHER INFORMATION: guide RNA 35T8P17

<400> SEQUENCE: 46
agttggagct gttggcg 17

<210> SEQ ID NO 47
<211> LENGTH: 20
<212> TYPE: DNA
<213> ORGANISM: Artificial Sequence
<220> FEATURE:
<223> OTHER INFORMATION: guide RNA 35T9P20

<400> SEQUENCE: 47
gtagttggag ctgttggcgt 20

<210> SEQ ID NO 48
<211> LENGTH: 17
<212> TYPE: DNA
<213> ORGANISM: Artificial Sequence
<220> FEATURE:
<223> OTHER INFORMATION: guide RNA 35T9P17

<400> SEQUENCE: 48
gttggagctg ttggcgt 17

<210> SEQ ID NO 49
<211> LENGTH: 20
<212> TYPE: DNA
<213> ORGANISM: Artificial Sequence
<220> FEATURE:
<223> OTHER INFORMATION: guide RNA 35T3M20

<400> SEQUENCE: 49
ttggcgtagg caagagtgcc 20

<210> SEQ ID NO 50
<211> LENGTH: 17
<212> TYPE: DNA
<213> ORGANISM: Artificial Sequence
<220> FEATURE:
<223> OTHER INFORMATION: guide RNA 35T3M17

<400> SEQUENCE: 50
ttggcgtagg caagagt 17

<210> SEQ ID NO 51
<211> LENGTH: 20
<212> TYPE: DNA
<213> ORGANISM: Artificial Sequence
<220> FEATURE:
<223> OTHER INFORMATION: guide RNA 35A3P20

<400> SEQUENCE: 51
cttgtggtag ttggagctga 20

<210> SEQ ID NO 52
<211> LENGTH: 17
<212> TYPE: DNA
<213> ORGANISM: Artificial Sequence
<220> FEATURE:
<223> OTHER INFORMATION: guide RNA 35A3P17

<400> SEQUENCE: 52
gtggtagttg gagctga 17

<210> SEQ ID NO 53
<211> LENGTH: 20
<212> TYPE: DNA
<213> ORGANISM: Artificial Sequence
<220> FEATURE:
<223> OTHER INFORMATION: guide RNA 35A8P20

<400> SEQUENCE: 53
ggtagttgga gctgatggcg 20

<210> SEQ ID NO 54
<211> LENGTH: 17
<212> TYPE: DNA
<213> ORGANISM: Artificial Sequence
<220> FEATURE:
<223> OTHER INFORMATION: guide RNA 35A8P17

<400> SEQUENCE: 54
agttggagct gatggcg 17

<210> SEQ ID NO 55
<211> LENGTH: 20
<212> TYPE: DNA
<213> ORGANISM: Artificial Sequence
<220> FEATURE:
<223> OTHER INFORMATION: guide RNA 35A9P20

-continued

<400> SEQUENCE: 55
gtagttggag ctgatggcgt 20

<210> SEQ ID NO 56
<211> LENGTH: 17
<212> TYPE: DNA
<213> ORGANISM: Artificial Sequence
<220> FEATURE:
<223> OTHER INFORMATION: guide RNA 35A9P17

<400> SEQUENCE: 56
gttggagctg atggcgt 17

<210> SEQ ID NO 57
<211> LENGTH: 20
<212> TYPE: DNA
<213> ORGANISM: Artificial Sequence
<220> FEATURE:
<223> OTHER INFORMATION: guide RNA 35A3M20

<400> SEQUENCE: 57
atggcgtagg caagagtgcc 20

<210> SEQ ID NO 58
<211> LENGTH: 17
<212> TYPE: DNA
<213> ORGANISM: Artificial Sequence
<220> FEATURE:
<223> OTHER INFORMATION: guide RNA 35A3M17

<400> SEQUENCE: 58
atggcgtagg caagagt 17

<210> SEQ ID NO 59
<211> LENGTH: 20
<212> TYPE: DNA
<213> ORGANISM: Artificial Sequence
<220> FEATURE:
<223> OTHER INFORMATION: guide RNA 38A6P20

<400> SEQUENCE: 59
gtagttggag ctggtgacgt 20

<210> SEQ ID NO 60
<211> LENGTH: 17
<212> TYPE: DNA
<213> ORGANISM: Artificial Sequence
<220> FEATURE:
<223> OTHER INFORMATION: guide RNA 38A6P17

<400> SEQUENCE: 60
gttggagctg gtgacgt 17

<210> SEQ ID NO 61
<211> LENGTH: 20
<212> TYPE: DNA
<213> ORGANISM: Artificial Sequence
<220> FEATURE:
<223> OTHER INFORMATION: guide RNA 38A5P20

<400> SEQUENCE: 61
ggtagttgga gctggtgacg 20

<210> SEQ ID NO 62
<211> LENGTH: 17

<212> TYPE: DNA
<213> ORGANISM: Artificial Sequence
<220> FEATURE:
<223> OTHER INFORMATION: guide RNA 38A5P17

<400> SEQUENCE: 62
agttggagct ggtgacg 17

<210> SEQ ID NO 63
<211> LENGTH: 20
<212> TYPE: DNA
<213> ORGANISM: Artificial Sequence
<220> FEATURE:
<223> OTHER INFORMATION: guide RNA 38A6M20

<400> SEQUENCE: 63
gtgacgtagg caagagtgcc 20

<210> SEQ ID NO 64
<211> LENGTH: 17
<212> TYPE: DNA
<213> ORGANISM: Artificial Sequence
<220> FEATURE:
<223> OTHER INFORMATION: guide RNA 38A6M17

<400> SEQUENCE: 64
gtgacgtagg caagagt 17

<210> SEQ ID NO 65
<211> LENGTH: 20
<212> TYPE: DNA
<213> ORGANISM: Artificial Sequence
<220> FEATURE:
<223> OTHER INFORMATION: guide RNA 34T4P20

<400> SEQUENCE: 65
cttgtggtag ttggagcttg 20

<210> SEQ ID NO 66
<211> LENGTH: 17
<212> TYPE: DNA
<213> ORGANISM: Artificial Sequence
<220> FEATURE:
<223> OTHER INFORMATION: guide RNA 34T4P17

<400> SEQUENCE: 66
gtggtagttg gagcttg 17

<210> SEQ ID NO 67
<211> LENGTH: 20
<212> TYPE: DNA
<213> ORGANISM: Artificial Sequence
<220> FEATURE:
<223> OTHER INFORMATION: guide RNA 34T9P20

<400> SEQUENCE: 67
ggtagttgga gcttgtggcg 20

<210> SEQ ID NO 68
<211> LENGTH: 17
<212> TYPE: DNA
<213> ORGANISM: Artificial Sequence
<220> FEATURE:
<223> OTHER INFORMATION: guide RNA 34T9P17

<400> SEQUENCE: 68
agttggagct tgtggcg 17

<210> SEQ ID NO 69
<211> LENGTH: 20
<212> TYPE: DNA
<213> ORGANISM: Artificial Sequence
<220> FEATURE:
<223> OTHER INFORMATION: guide RNA 34T10P20

<400> SEQUENCE: 69
gtagttggag cttgtggcgt 20

<210> SEQ ID NO 70
<211> LENGTH: 17
<212> TYPE: DNA
<213> ORGANISM: Artificial Sequence
<220> FEATURE:
<223> OTHER INFORMATION: guide RNA 34T10P17

<400> SEQUENCE: 70
gttggagctt gtggcgt 17

<210> SEQ ID NO 71
<211> LENGTH: 20
<212> TYPE: DNA
<213> ORGANISM: Artificial Sequence
<220> FEATURE:
<223> OTHER INFORMATION: guide RNA 34C4P20

<400> SEQUENCE: 71
cttgtggtag ttggagctcg 20

<210> SEQ ID NO 72
<211> LENGTH: 17
<212> TYPE: DNA
<213> ORGANISM: Artificial Sequence
<220> FEATURE:
<223> OTHER INFORMATION: guide RNA 34C4P17

<400> SEQUENCE: 72
gtggtagttg gagctcg 17

<210> SEQ ID NO 73
<211> LENGTH: 20
<212> TYPE: DNA
<213> ORGANISM: Artificial Sequence
<220> FEATURE:
<223> OTHER INFORMATION: guide RNA 34C9P20

<400> SEQUENCE: 73
ggtagttgga gctcgtggcg 20

<210> SEQ ID NO 74
<211> LENGTH: 17
<212> TYPE: DNA
<213> ORGANISM: Artificial Sequence
<220> FEATURE:
<223> OTHER INFORMATION: guide RNA 34C9P17

<400> SEQUENCE: 74
agttggagct cgtggcg 17

<210> SEQ ID NO 75
<211> LENGTH: 20
<212> TYPE: DNA
<213> ORGANISM: Artificial Sequence
<220> FEATURE:
<223> OTHER INFORMATION: guide RNA 34C10P20

<400> SEQUENCE: 75
gtagttggag ctcgtggcgt 20

<210> SEQ ID NO 76
<211> LENGTH: 17
<212> TYPE: DNA
<213> ORGANISM: Artificial Sequence
<220> FEATURE:
<223> OTHER INFORMATION: guide RNA 34C10P17

<400> SEQUENCE: 76
gttggagctc gtggcgt 17

<210> SEQ ID NO 77
<211> LENGTH: 20
<212> TYPE: DNA
<213> ORGANISM: Artificial Sequence
<220> FEATURE:
<223> OTHER INFORMATION: guide RNA 35C3M20

<400> SEQUENCE: 77
ctggcgtagg caagagtgcc 20

<210> SEQ ID NO 78
<211> LENGTH: 17
<212> TYPE: DNA
<213> ORGANISM: Artificial Sequence
<220> FEATURE:
<223> OTHER INFORMATION: guide RNA 35C3M17

<400> SEQUENCE: 78
ctggcgtagg caagagt 17

<210> SEQ ID NO 79
<211> LENGTH: 20
<212> TYPE: DNA
<213> ORGANISM: Artificial Sequence
<220> FEATURE:
<223> OTHER INFORMATION: guide RNA 35C3P20

<400> SEQUENCE: 79
cttgtggtag ttggagctgc 20

<210> SEQ ID NO 80
<211> LENGTH: 17
<212> TYPE: DNA
<213> ORGANISM: Artificial Sequence
<220> FEATURE:
<223> OTHER INFORMATION: guide RNA 35C3P17

<400> SEQUENCE: 80
gtggtagttg gagctgc 17

<210> SEQ ID NO 81
<211> LENGTH: 20
<212> TYPE: DNA
<213> ORGANISM: Artificial Sequence
<220> FEATURE:
<223> OTHER INFORMATION: guide RNA 35C8P20

<400> SEQUENCE: 81
ggtagttgga gctgctggcg 20

<210> SEQ ID NO 82
<211> LENGTH: 17
<212> TYPE: DNA
<213> ORGANISM: Artificial Sequence
<220> FEATURE:
<223> OTHER INFORMATION: guide RNA 35C8P17

<400> SEQUENCE: 82
agttggagct gctggcg 17

<210> SEQ ID NO 83
<211> LENGTH: 20
<212> TYPE: DNA
<213> ORGANISM: Artificial Sequence
<220> FEATURE:
<223> OTHER INFORMATION: guide RNA 35C9P20

<400> SEQUENCE: 83
gtagttggag ctgctggcgt 20

<210> SEQ ID NO 84
<211> LENGTH: 17
<212> TYPE: DNA
<213> ORGANISM: Artificial Sequence
<220> FEATURE:
<223> OTHER INFORMATION: guide RNA 35C9P17

<400> SEQUENCE: 84
gttggagctg ctggcgt 17

<210> SEQ ID NO 85
<211> LENGTH: 39
<212> TYPE: DNA
<213> ORGANISM: Artificial Sequence
<220> FEATURE:
<223> OTHER INFORMATION: Wild-type KRAS sequence

<400> SEQUENCE: 85
cttgtggtag ttggagctgg tggcgtaggc aagagtgcc 39

<210> SEQ ID NO 86
<211> LENGTH: 29
<212> TYPE: DNA
<213> ORGANISM: Artificial Sequence
<220> FEATURE:
<223> OTHER INFORMATION: Wild-type KRAS sequence

<400> SEQUENCE: 86
cttgtggtag ttggagctgg tggcgtagg 29

<210> SEQ ID NO 87
<211> LENGTH: 39
<212> TYPE: DNA
<213> ORGANISM: Artificial Sequence
<220> FEATURE:
<223> OTHER INFORMATION: c.35G>T mutant KRAS sequence

<400> SEQUENCE: 87
cttgtggtag ttggagctgt tggcgtaggc aagagtgcc 39

<210> SEQ ID NO 88
<211> LENGTH: 39
<212> TYPE: DNA
<213> ORGANISM: Artificial Sequence
<220> FEATURE:
<223> OTHER INFORMATION: c.35G>A mutant KRAS sequence -continued

```
<400> SEQUENCE: 88

cttgtggtag ttggagctga tggcgtaggc aagagtgcc                          39


<210> SEQ ID NO 89
<211> LENGTH: 39
<212> TYPE: DNA
<213> ORGANISM: Artificial Sequence
<220> FEATURE:
<223> OTHER INFORMATION: c.38G>A mutant KRAS sequence

<400> SEQUENCE: 89

cttgtggtag ttggagctgg tgacgtaggc aagagtgcc                          39


<210> SEQ ID NO 90
<211> LENGTH: 29
<212> TYPE: DNA
<213> ORGANISM: Artificial Sequence
<220> FEATURE:
<223> OTHER INFORMATION: c.34G>T mutant KRAS sequence

<400> SEQUENCE: 90

cttgtggtag ttggagcttg tggcgtagg                                     29


<210> SEQ ID NO 91
<211> LENGTH: 29
<212> TYPE: DNA
<213> ORGANISM: Artificial Sequence
<220> FEATURE:
<223> OTHER INFORMATION: c.34G>C mutant KRAS sequence

<400> SEQUENCE: 91

cttgtggtag ttggagctcg tggcgtagg                                     29


<210> SEQ ID NO 92
<211> LENGTH: 39
<212> TYPE: DNA
<213> ORGANISM: Artificial Sequence
<220> FEATURE:
<223> OTHER INFORMATION: c.35G>C mutant KRAS sequence

<400> SEQUENCE: 92

cttgtggtag ttggagctgc tggcgtaggc aagagtgcc                          39
```

GUIDE RNA COMPLEMENTARY TO KRAS GENE, AND USE THEREOF

TECHNICAL FIELD

The present disclosure relates to a guide RNA complementary to a KRAS gene, a vector including the guide RNA, a composition for removing a nucleotide sequence encoding a KRAS polypeptide in the genome of a cell, the composition including the guide RNA, a composition for preventing or treating a cancer, the composition including the guide RNA, and a method of using the guide RNA.

BACKGROUND ART

A term "molecular scissors" refers to an enzyme that binds to a gene to cleave a specific DNA site. Genome editing technique uses the molecular scissors, Molecular scissors may be used in a variety of fields such as correction of a molecular disease-causing mutation in stem cells or somatic cells and cancer cell therapy. Known molecular scissors includes zinc finger nuclease (ZFN), transcriptional activator-like effector nuclease (TALEN), type II clustered regularly interspaced repeat/CRISPR-associated (CRISPR/Cas) which are RNA-guided engineered nucleases (RGENs) derived from the prokaryotic adaptive immune system, etc. Delivery of Cas9 nuclease and an appropriate guide RNA into a cell may cleave a target site in the genome of the cell to remove the existing gene and to insert a new gene. When a specific DNA is cleaved using the molecular scissors, Cas9 nuclease cleaves the DNA target sequence specified by a sequence of guide RNA. Methods of genome editing using molecular scissors are known in many literatures such as Korean Patent Publication No. 10-2015-0101478 (published in Sep. 3, 2015), etc.

KRAS is one of oncogenes frequently mutated in human tumors. Normal KRAS performs an essential function in normal tissue signaling. However, since mutations of the KRAS gene are involved in the development of many cancers, it is an important therapeutic target.

Accordingly, in order to specifically remove the KRAS gene mutant, it is necessary to develop a guide DNA targeting the KRAS gene mutant.

DESCRIPTION OF EMBODIMENTS

Technical Problem

Provided is a guide RNA including two or more consecutive polynucleotides complementary to a target nucleotide sequence encoding a KRAS polypeptide.

Provided is a vector including the guide RNA.

Provided is a composition for removing the nucleotide sequence encoding the KRAS polypeptide in the genome of a cell.

Provided is a pharmaceutical composition for preventing or treating a cancer.

Provided is a method of mutating the nucleotide sequence encoding the KRAS polypeptide in the genome of a cell.

Provided is a method of preventing or treating a cancer.

Solution to Problem

An aspect provides a guide RNA including two or more consecutive polynucleotides complementary to a target nucleotide sequence encoding a KRAS polypeptide.

The KRAS polypeptide may be a wild-type KRAS polypeptide or a mutant KRAS polypeptide. The wild-type KRAS polypeptide may include, in the case of humans, an amino acid sequence of GenBank Accession No. NP_203524.1. The wild-type KRAS polypeptide may include, in the case of humans, an amino acid sequence encoded by a nucleotide sequence of GenBank Accession No. NM_033360.3.

The target nucleotide sequence may have a modification of a nucleotide at position 34, a nucleotide at position 35, or a nucleotide at position 38 from the 5'-terminus of the nucleotide sequence encoding the wild-type KRAS polypeptide, or a combination thereof. The polynucleotide may have a modification from guanine (G) to thymine (T) or cytosine (C) at position 34, a modification from guanine (G) to any one of thymine (T), adenine (A), and cytosine (C) at position 35, or a modification from guanine (G) to adenine (A) at position 38.

The target nucleotide sequence may include a protospacer adjacent motif (PAM). The PAM may be a site that is specifically recognized by Cas9 nuclease. The PAM may include a nucleotide sequence selected from the group consisting of 5'-TGG-3', 5'-TAG-3", 5'-AGG-3', and 5'-CTG-3'.

The target nucleotide sequence may include a nucleotide sequence identical or complementary to a nucleotide sequence selected from the group consisting of SEQ ID NOS: 1 to 42.

The term "guide RNA" refers to a polynucleotide that cleaves, inserts, or links a target DNA in a cell via RNA editing. The guide RNA may be a single-chain guide RNA (sgRNA). The guide RNA may be a CRISPR RNA (crRNA) specific to the target nucleotide sequence. The guide RNA may further include a trans-activating crRNA (tracrRNA) interacting with Cas9 nuclease. The tracrRNA may include a polynucleotide forming a loop structure. The guide RNA may have a length of 10 nucleotides to 30 nucleotides. The guide RNA may have a length of, for example, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides.

The guide RNA may include a nucleotide sequence identical or complementary to two or more consecutive polynucleotides in a nucleotide sequence selected from the group consisting of SEQ ID NOS: 42 to 84. The guide RNA may include two or more consecutive polynucleotides complementary to a nucleotide sequence other than the PAM sequence in a target nucleotide sequence selected from the group consisting of SEQ ID NOS: 1 to 42. The guide RNA may be a polynucleotide complementary to a nucleotide sequence other than the PAM sequence in a target nucleotide sequence selected from the group consisting of SEQ ID NOS: 1 to 42.

The guide RNA may include RNA, DNA, PNA, or a combination thereof. The guide RNA may be chemically modified.

The guide RNA may be a component of molecular scissors (programmable nuclease). The molecular scissor refers to all types of nucleases capable of recognizing and cleaving a specific site on the genome. The molecular scissors may be, for example, transcription activator-like effector nuclease (TALEN), zinc-finger nuclease, meganuclease, RNA-guided engineered nuclease (RGEN), Cpf1, and Ago homolog (DNA-guided endonuclease). The RGEN refers to a nuclease including a guide RNA specific to a target DNA and Gas protein as components. The polynucleotide may be, for example, a component of RGEN.

The guide RNA may remove the nucleotide sequence encoding the KRAS polypeptide from the genome of a cell by non-homologous end-joining (NHEJ).

Another aspect provides a vector including the guide RNA of an aspect.

The vector may be a viral vector. The viral vector may be a lentiviral vector or an adeno-associated viral (AAV) vector. The vector may be an expression vector. The vector may be a constitutive or inducible expression vector. The vector may include a packaging signal, rev response element (RRV), Woodchuck hepatitis virus post-transcriptional regulatory element (WPRE), central polypurine tract (cPPT), a promoter, an antibiotic resistance gene, an operator, a suppressor, a T2A peptide, a reporter gene, or a combination thereof. The promoter may include a U6 polymerase Ill promoter, an elongation factor 1$\alpha$ promoter, an H1 promoter, a promoter of cytomegalovirus, or a combination thereof. The antibiotic resistance gene may include a puromycin resistance gene, a blasticidin resistance gene, or a combination thereof. The suppressor may include a tetracycline operator. The reporter gene may include a nucleotide sequence encoding an enhanced green fluorescent protein.

Still another aspect provides a composition for removing the nucleotide sequence encoding the KRAS polypeptide from the genome of a cell, the composition including the guide RNA according to an aspect, the vector according to an aspect, or a combination thereof.

The guide RNA, the vector, the KRAS polypeptide, and the nucleotide sequence encoding the KRAS polypeptide are the same as described above.

The cell may be selected from the group consisting of cancer cells, stem cells, vascular endothelial cells, white blood cells, immune cells, epithelial cells, germ cells, fibroblasts, muscle cells, bone marrow cells, epidermal cells, osteoblasts, and nerve cells.

The "removing" refers to all modifications whereby the function of the KRAS polypeptide is lost or reduced by modification of the nucleotide sequence encoding the KRAS polypeptide in the genome of a cell. The term "removing" may be interchangeable with "mutation". The removing or mutation may be, for example, deletion, substitution, insertion, or frame-shift mutation.

The composition may be for in vitro or in vivo administration.

The composition may further include a second polynucleotide including a nucleotide sequence encoding a Cas polypeptide. The Cas polypeptide is one of protein components of CRISPR/Cas system, and may be an activated endonuclease or a nicking enzyme. The Cas polypeptide may exhibit its activity after forming a complex with CRISPR RNA (crRNA) and trans-activating crRNA (tracrRNA).

The Cas polynucleotide may be a polynucleotide derived from a bacterium, for example, the genus *Streptococcus* (e.g., *Streptococcus pyogenes*), the genus *Neisseria* (e.g. *Neisseria meningitidis*), the genus *Pasteurella* (e.g., *Pasteurella multocida*), the genus *Francisella* (e.g., *Francisella novicida*), or the genus Campylobacter (e.g., Campylobacter jejuni). The Cas polypeptide may include an amino acid sequence of GenBank Accession No, Q99ZW2.1. The Cas polypeptide may include an amino acid sequence encoded by a nucleotide sequence of GenBank Accession No. KT031982.1.

The Cas polypeptide may be a wild-type Cas polypeptide or a mutant Cas polypeptide. The mutant Cas polypeptide may be, for example, a polypeptide in which a catalytic aspartate residue is modified to another amino acid (e.g., alanine). The Cas polypeptide may be a recombinant protein.

The Cas polypeptide may be a Cas9 polypeptide or a Cpf1 polypeptide.

Still another aspect provides a composition for preventing or treating a cancer, the composition including the guide RNA according to an aspect, the vector according to an aspect, or a combination thereof.

The guide RNA and the vector are the same as described above.

The cancer may be a primary tumor or a metastatic tumor. The cancer may be, for example, selected from the group consisting of pancreatic cancer, colon cancer, lung cancer, breast cancer, skin cancer, head and neck cancer, colorectal cancer, stomach cancer, ovarian cancer, prostate cancer, bladder cancer, urethral cancer, liver cancer, kidney cancer, clear cell sarcoma, melanoma, cerebrospinal tumor, brain cancer, thymoma, mesothelioma, esophageal cancer, biliary cancer, testicular cancer, germ cell tumor, thyroid cancer, parathyroid cancer, cervical cancer, endometrial cancer, lymphoma, myelodysplastic syndromes (MDS), myelofibrosis, acute leukemia, chronic leukemia, multiple myeloma, Hodgkin's disease, neuroendocrine tumor, and sarcoma.

The term "preventing" refers to all of actions by which occurrence of the cancer is restrained or retarded by administration of the pharmaceutical composition. The term "treating" refers to all of actions by which symptoms of the cancer have taken a turn for the better or been modified favorably by administration of the pharmaceutical composition.

The pharmaceutical composition may further include a second polynucleotide including the nucleotide sequence encoding the Cas polypeptide. The guide RNA according to an aspect, the vector according to an aspect, or a combination thereof and the second polynucleotide may be a single composition or a separate composition.

The pharmaceutical composition may further include a pharmaceutically acceptable carrier. The carrier may be used as a meaning including an excipient, a diluent, or an additive. The carrier may be, for example, selected from the group consisting of lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinyl pyrrolidone, water, physiological saline, buffers such as PBS, methylhydroxy benzoate, propylhydroxy benzoate, talc, magnesium stearate, and mineral oil. The composition may include a filler, an anticoagulant, a lubricant, a wetting agent, a flavor, an emulsifier, a preservative, or a combination thereof.

The pharmaceutical composition may be prepared in any formulation according to a common method. The composition may be prepared in, for example, an oral formulation (e.g powder, tablet, capsule, syrup, pill, or granule) or a parenteral formulation (e.g., injectable formulation). Further, the composition may be prepared in a systemic formulation or a topical formulation. The pharmaceutical composition may be administered orally, intravenously, intramuscularly, transdermally, mucosally, intranasally, intratracheally, subcutaneously, or by a combination thereof.

The pharmaceutical composition may include an effective amount of the guide RNA or the vector according to an aspect or a combination thereof. The term "effective amount" refers to an amount sufficient to exhibit the prophylactic or therapeutic effects when administered to a subject in need of prophylactic or therapeutic treatment. The effective amount may be appropriately selected depending on a cell or a subject selected by those skilled in the art. The effective amount may be determined depending on factors including severity of the disease, a patient's age, body weight, health, sex, sensitivity to the drug, administration time, administration route, excretion rate, duration of treatment, a drug blended with or concurrently used with the composition, and other factors well known in the medical arts. The effective amount may be about 0.1 μg to about 2 g, about 0.5 μg to about 1 g, about 1 μg to about 500 mg, about 10 μg to about 100 mg, or about 100 μg to about 50 mg per the pharmaceutical composition.

An administration dose of the pharmaceutical composition may be, for example, in the range of about 0.001 mg/kg to about 100 mg/kg, about 0.01 mg/kg to about 10 mg/kg, or about 0.1 mg/kg to about 1 mg/kg per adult. The administration may be performed once a day, several times a day, or once a week, once every two weeks, once every three weeks, or once every four weeks to once a year.

Still another aspect provides a method of mutating the nucleotide sequence encoding the KRAS polypeptide in the genome of a cell, the method including incubating the cell with the guide RNA according to an aspect, the vector according to an aspect, or a combination thereof.

The guide RNA, the vector, the cell, the KRAS polypeptide, the nucleotide sequence encoding the KRAS polypeptide, and the mutation are the same as described above.

The incubating may be performed in vitro or in vivo.

The method may further include second incubating the cell with the second polynucleotide including the nucleotide sequence encoding the Cas polypeptide. The second incubating may be performed concurrently with, before, or after incubating the cell with the guide RNA according to an aspect, the vector according to an aspect, or a combination thereof.

Still another aspect provides a method of preventing or treating a cancer, the method including administering to a subject the guide RNA according to an aspect, the vector according to an aspect, or a combination thereof.

The subject may be a subject having the genome including the nucleotide sequence encoding the mutant KRAS polypeptide. The subject may be a mammal, for example, a human, a cow, a horse, a pig, a dog, a sheep, a goat, or a cat. The subject may be a subject suffering from the cancer or at a high risk of suffering from the cancer.

The guide RNA, the vector, or a combination thereof may be administered orally, intravenously, intramuscularly, transdermally, mucosally, intranasally, intratracheally, or subcutaneously. An appropriate administration dose of the polynucleotide, the vector, or a combination thereof may vary depending on a patient's conditions and body weight, disease severity, drug type, administration route and time, but may be appropriately selected by those skilled in the art. The administration dose may be, for example, in the range of about 0.001 mg/kg to about 100 mg/kg, about 0.01 mg/kg to about 10 mg/kg, or about 0.1 mg/kg to about 1 mg/kg per adult. The administration may be performed once a day, several times a day, or once a week, once every two weeks, once every three weeks, or once every four weeks to once a year.

Advantageous Effects of Disclosure

A guide RNA according to an aspect, a vector including the guide RNA, a composition for removing a nucleotide sequence encoding a KRAS polypeptide in the genome of a cell, the composition including the guide RNA, a composition for preventing or treating a cancer, the composition including the guide RNA, and a method of using the guide RNA may be used in mutating the nucleotide sequence encoding the KRAS polypeptide in the genome of a cell or a subject, and particularly, used for preventing or treating a cancer in personalized or precision medical care.

BRIEF DESCRIPTION OF DRAWINGS

FIGS. 2A to 2F show graphs (left) showing a percentage (%) of cells expressing both mRFP and eGFP relative to that of cells expressing only mRFP, and target sequences of each guide RNA (right, arrows and bold letters: target KRAS mutant, bold letters: PAM sequence);

MODE OF DISCLOSURE

Hereinafter, the present disclosure will be described in more detail with reference to Examples. However, these Examples are provided only for illustrating one or more specific embodiments, and the scope of the present disclosure is not intended to be limited by these Examples.

Example 1. Screening and Identification of Guide RNA

1. Selection of Target KRAS Mutants

Figure 1A:
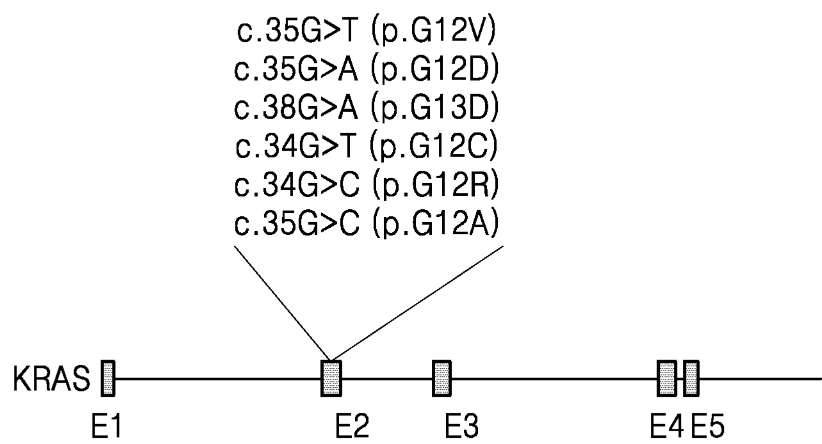
FIG. 1A illustrates KRAS mutations on the human genome strongly associated with cancer development.

KRAS gene on the human genome is known to have five exons. KRAS mutants on the human genome strongly associated with cancer development are illustrated in FIG. 1A. In FIG. 1A, "E" represents an exon, and "E2" represents an exon 2. As shown in FIG. 1A, six KRAS point mutations located in exon 2 of KRAS gene (GRCh38.p7 (GCF_000001405.33)) were selected as targets. The selected KRAS point mutations were c.35G>T (p.G12V), c.35G>A (p.G12D), c.38G>A (p.G13D), c.34G>T (p.G12C), c.34G>C (p.G12R), and c.35G>C (p.G12A). For example, "c.35G>T (p.G12V)" means that a nucleotide at position 35 from the 5-terminus of the KRAS gene is mutated from guanine (G) to thymine (T), and an amino acid at position 12 from the M-terminal of an amino acid sequence of the KRAS protein is mutated from glycine (G) to valine (V).

2. Preparation of Vector for Guide RNA Selection

To select guide RNA, the guide RNA was named as a total of 7 letters. In FIGS. 2A to 2F, target sequences of each guide RNA are shown (right). In FIGS. 2A to 2F, target KRAS mutations are indicated by arrows and bold letters, and PAM sequence (5'-TGG-3', 5'-TAG-3', 5'-AGG-3', or 5-CTG-3') is indicated by bold letters. The first three letters in the name of guide RNA represent the target KRAS mutation, and when the target KRAS mutation is c.35G>T, it is expressed as "35T". The fourth letter represents a distance (bp) from PAM to the mutation site. The fifth letter represents the position of PAM relative to the mutation site. When the mutation site is located on the left of PAM, it is expressed as P (plus). When the mutation site is located on the right of PAM, it is expressed as M (minus). The sixth and seventh letters indicate a length (bp) of the guide RNA, excluding the PAM sequence. For example, "35T9P17" means that the KRAS mutation c.35G>T is targeted, a distance from the mutation site to PAM is 9 bp, the mutation is located on the left of PAM, and a length of the guide RNA, excluding the PAM sequence, is 17 bp. Each guide RNA was designed to have a sequence complementary to a nucleotide sequence other than the PAM sequence in the target sequence.

Figure 1B:
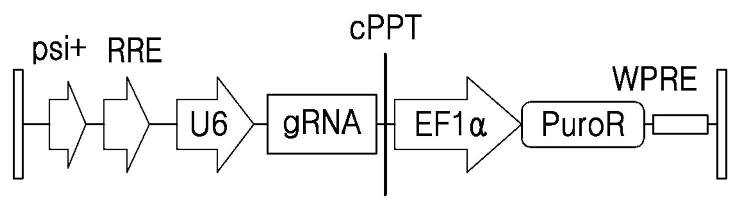
FIG. 1B illustrates a surrogate NHEJ reporter system.
Figure 1B:
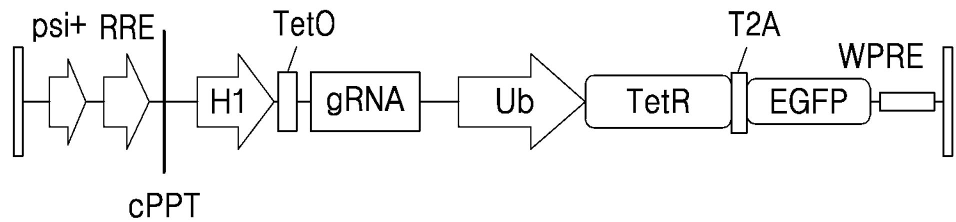
Figure 1B:
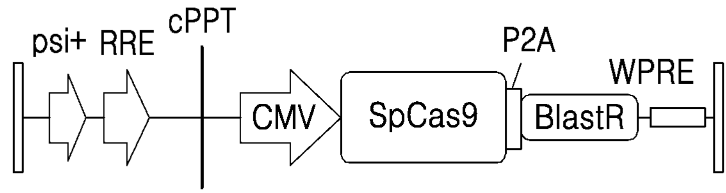

To evaluate guide RNA (sgRNA) activity, a surrogate NHEJ reporter system was used (Kim, H. et at, Nature methods, vol. 8, pp. 941-943, published in 2011; and Nature communications, vol. 5, p. 3378, 2014). The used surrogate NHEJ reporter system is illustrated in FIG. 1B, In FIG. 1B, "lenti_gRNA-pure" represents a lentiviral vector that constitutively expresses guide RNA (guide RNA: sgRNA), "lenti_gRNA-doxy-inducible_GFP" represents an inducible lentiviral vector that expresses guide RNA in a doxycycline-inducible manner, and lenti_SpCas9-Blast represents a lentiviral vector that expresses Cas9 nuclease (Psi: packaging signal, RRE: rev response element, WPRE: Woodchuck hepatitis virus post-transcriptional regulatory element (WPRE), cPPT: central polypurine tract, U6: polymerase III promoter, gRNA: guide RNA, EF1α: elongation factor 1α promoter, PuroR: puromycin resistance gene, H1:H1 promoter, TetO: tetracycline operator, Ub: ubiquitin promoter, TetR: tetracycline suppressor, T2A: T2A peptide, EGFP: enhanced green fluorescent protein, CMV: cytomegalovirus promoter, BlastR: blasticidin resistance gene).

Figure 1C:
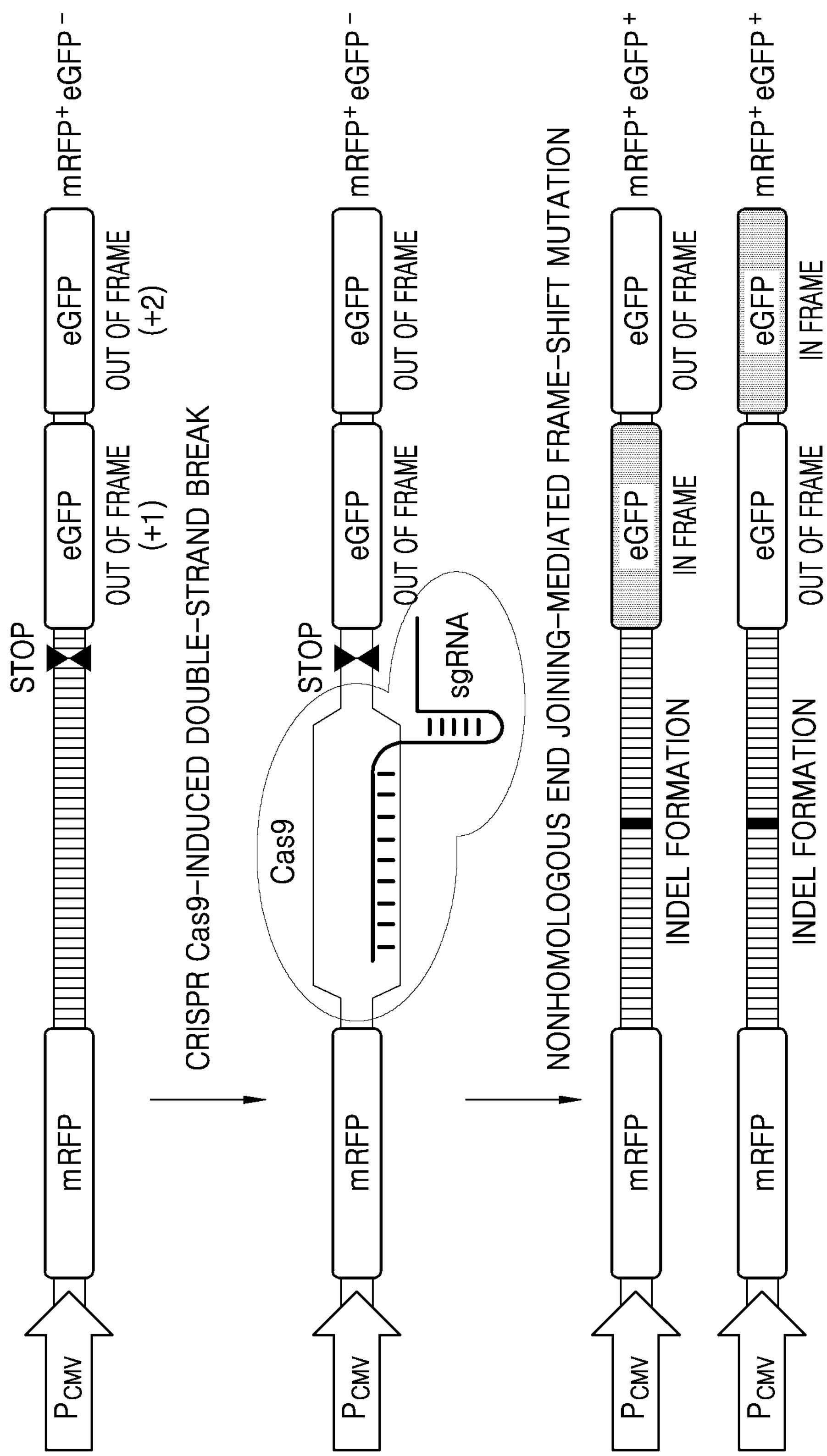
FIG. 1C illustrates a mechanism of action of the prepared surrogate NHEJ reporter system.
Figure 2A:
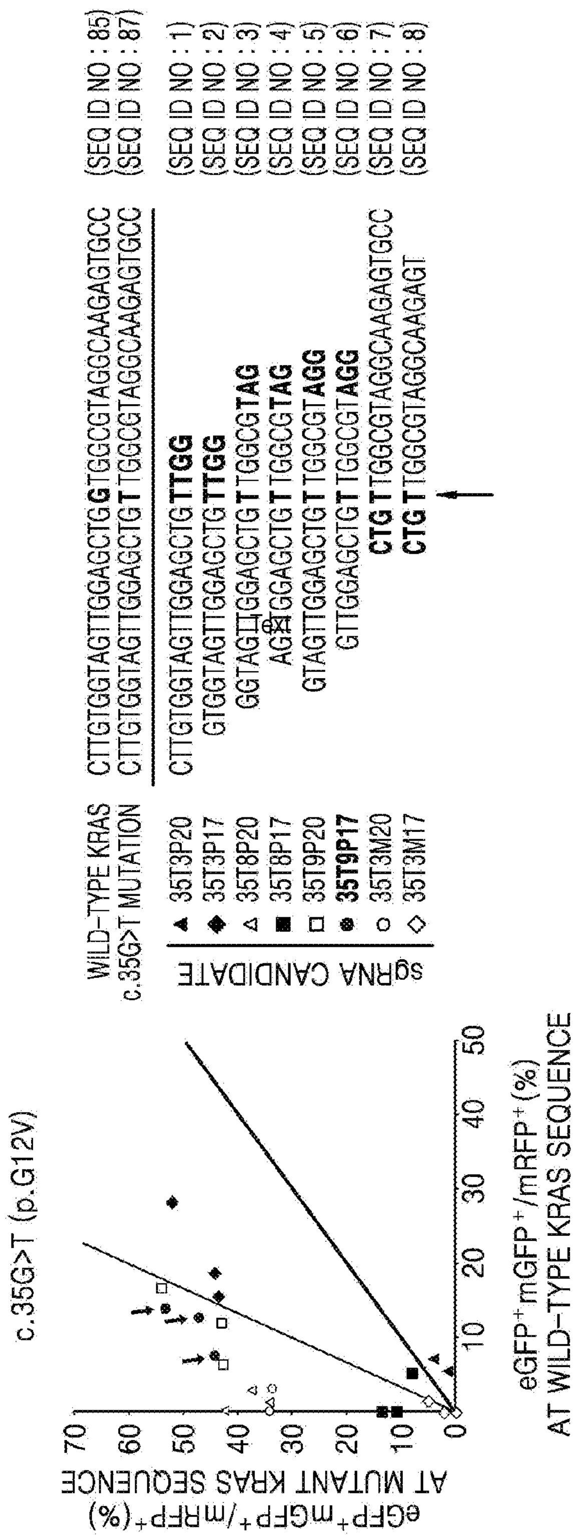
Figure 2B:
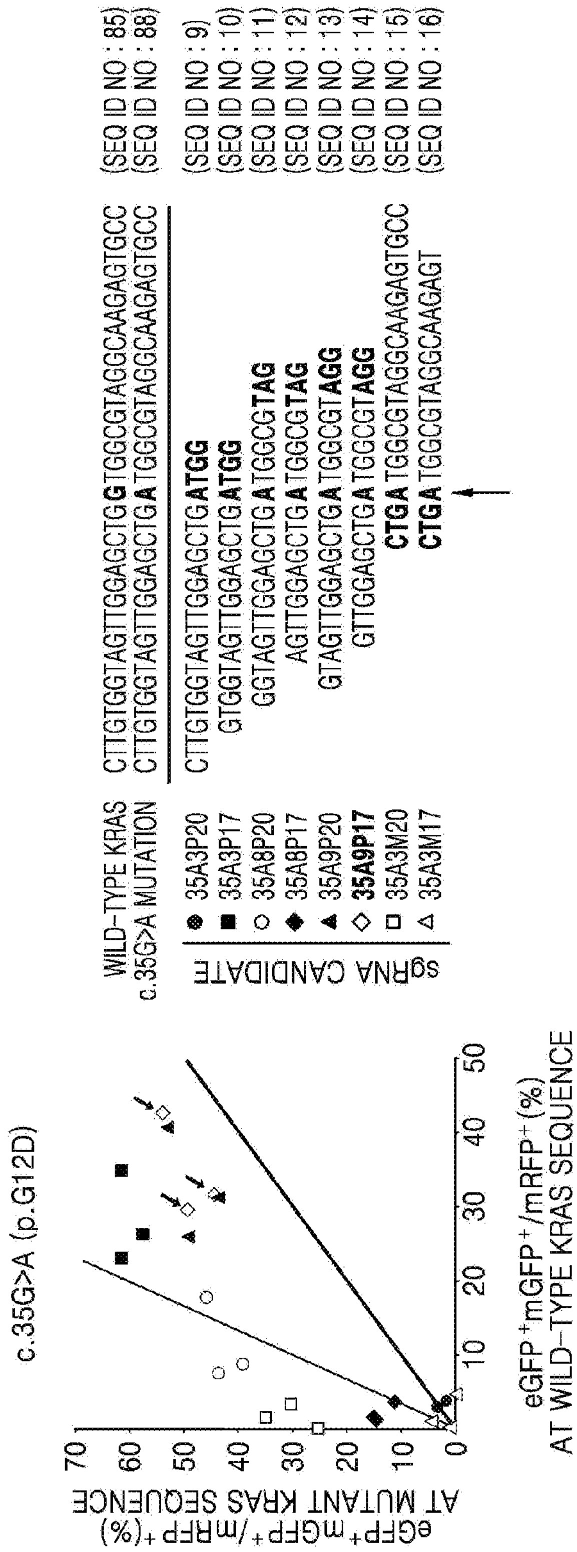
Figure 2C:
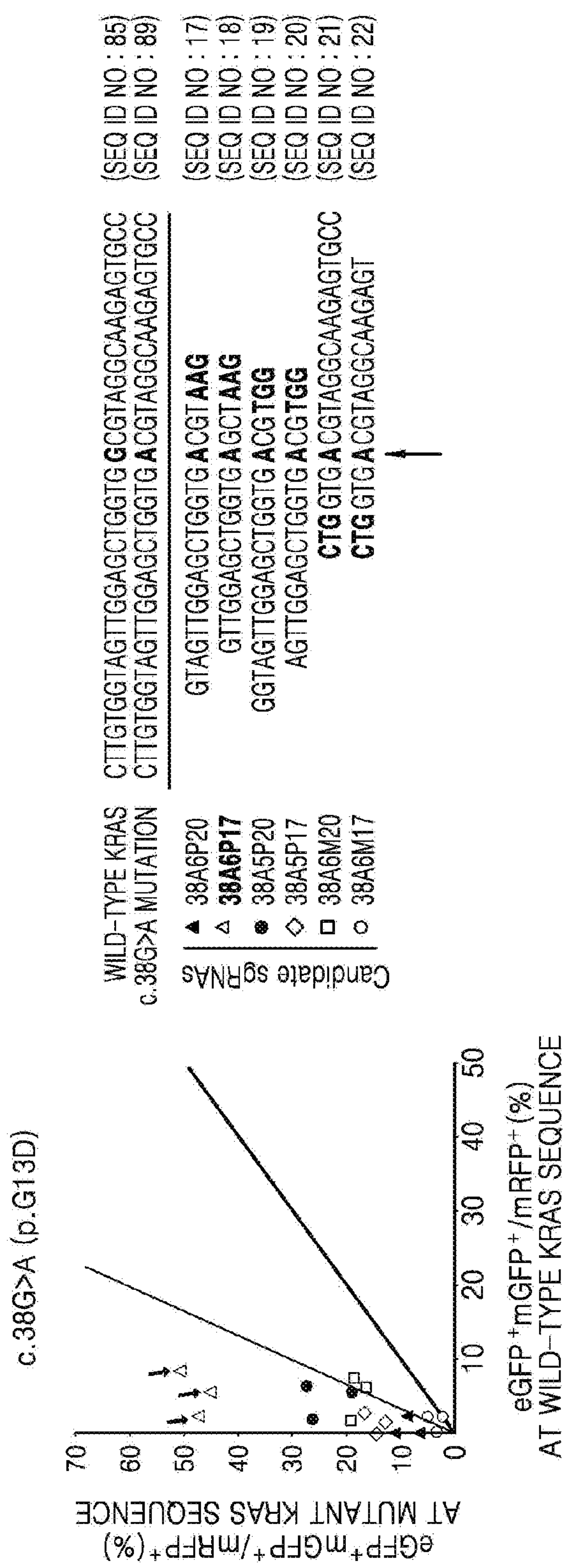
Figure 2D:
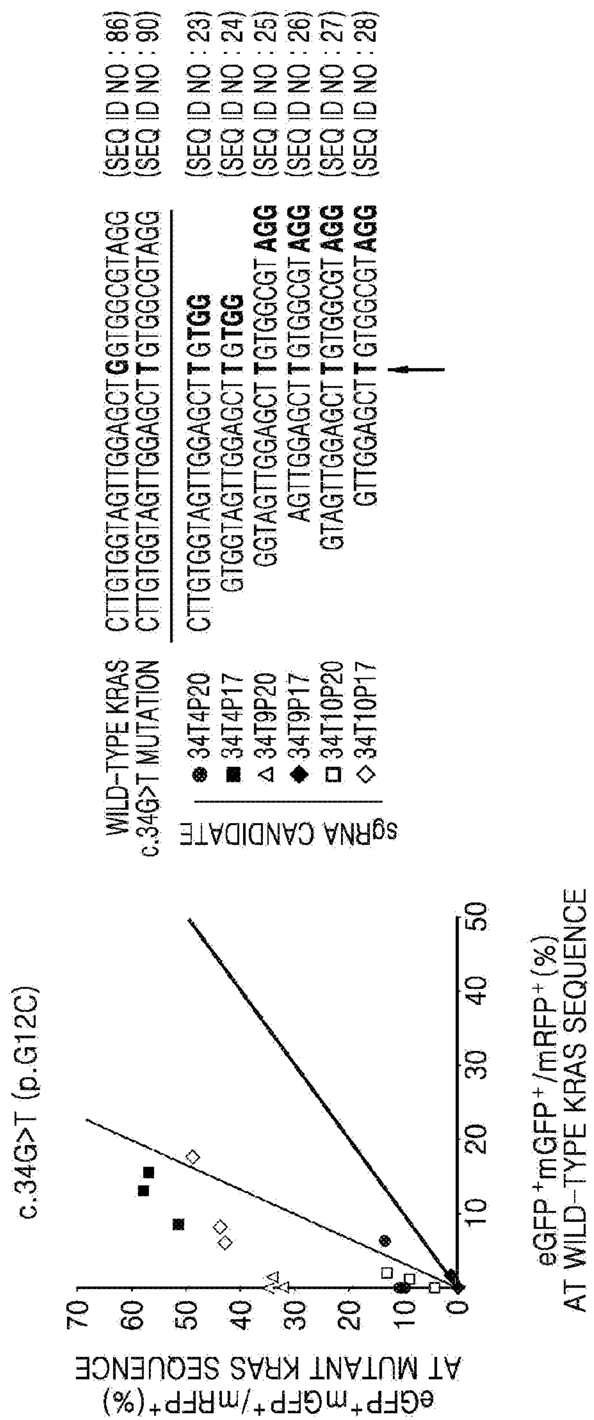
Figure 2F:
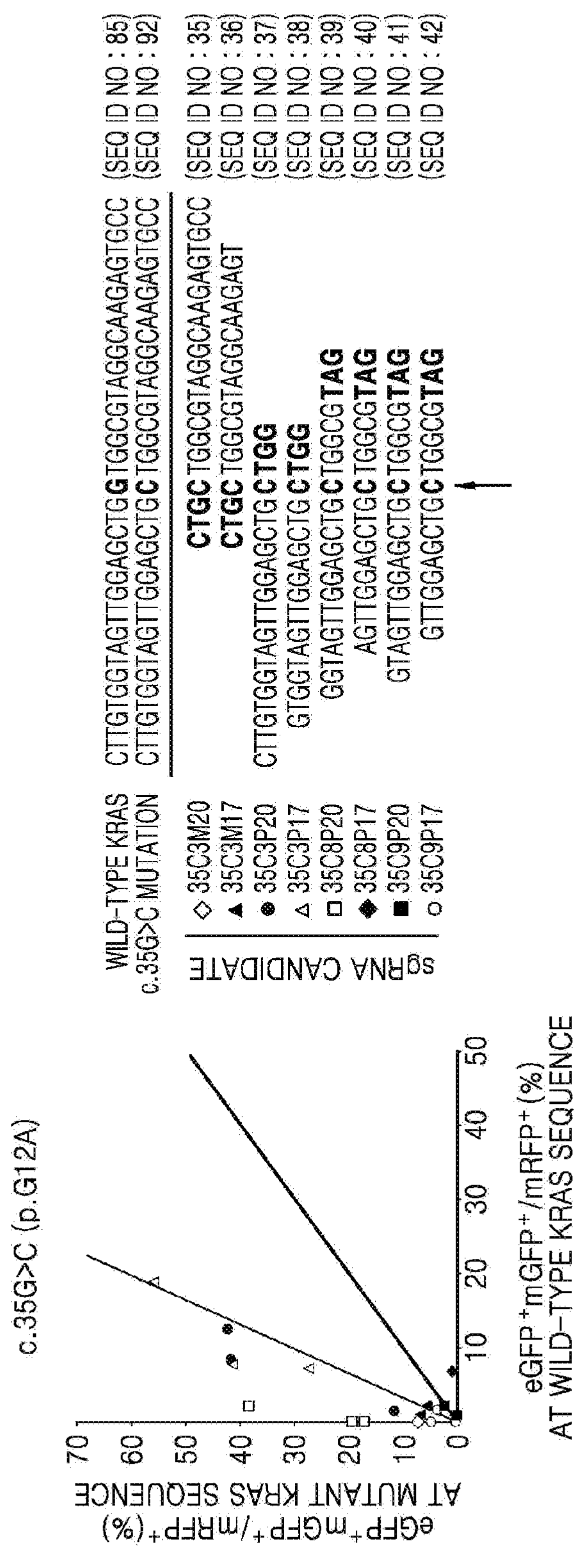

A mechanism of action of the prepared surrogate NHEJ reporter system is shown in FIG. 1C. As shown in FIG. 1C, the monomeric red fluorescent protein (mRFP) was constitutively expressed by the CMV promoter ($P_{CMV}$), and the enhanced green fluorescent protein (eGFP) was not expressed without the CRISPR/Cas9 activity because it was not in frame. When a double-strand break is introduced into the target sequence by CRISPR/Cas9, this break is repaired by error-prone nonhomologous end joining, leading to insertion/deletion (indel) formation. This indel formation causes frame-shifting of two eGFP genes, leading to eGFP expression.

3. Screening of Guide RNA

To select guide RNAs specifically recognizing target KRAS mutations, a reporter plasmid including the wild-type KRAS sequence or the mutant KRAS sequence, a plasmid encoding Cas9, and a plasmid encoding the guide RNA were co-transfected into HEK293T cells. The transfected cells were subjected to flow cytometry to determine the percentage of cells expressing both mRFP and eGFP normalized to that of cells expressing only mRFP. The results are shown in the left graphs of FIGS. 2A to 2F. This percentage represents the activity of the guide RNA on the target sequence. In the left graphs of FIGS. 2A to 2F, thick and thin lines represent ratios of $eGFP^{+}mRFP^{+}/mRFP^{+}$ cells for mutant KRAS sequences vs. wild-type KRAS sequences with values of 1 and 3, respectively. The target sequence of each guide RNA is shown on the right side, the KRAS point mutation site is indicated by arrow and in bold, and the protospacer adjacent motif (PAM) is in bold.

As shown in the right graphs of FIGS. 2A to 2F, some guide RNAs resulted in high GFP expression with the mutant KRAS sequence and low expression with the wild-type KRAS sequence, suggesting that they were guide RNAs specific to the mutant KRAS sequences. The guide RNAs primarily selected are indicated by arrows in the left graphs of FIGS. 2A to 2F. Two guide RNAs (35T9P17 and 38A6P17) with high selectivity and one guide RNA (35A9P17) with low selectivity for mutant KRAS were secondarily selected, and the name of each selected guide RNA is shown in bold in the right of FIGS. 2A to 2F.

4. Validation of Functions of Selected Guide RNAs

To validate the function of the guide RNAs selected in 3. at the endogenous target KRAS sequences, cancer cells having KRAS mutations were transduced with lentiviral vectors encoding Cas9 and the corresponding guide RNAs.

Figure 3:
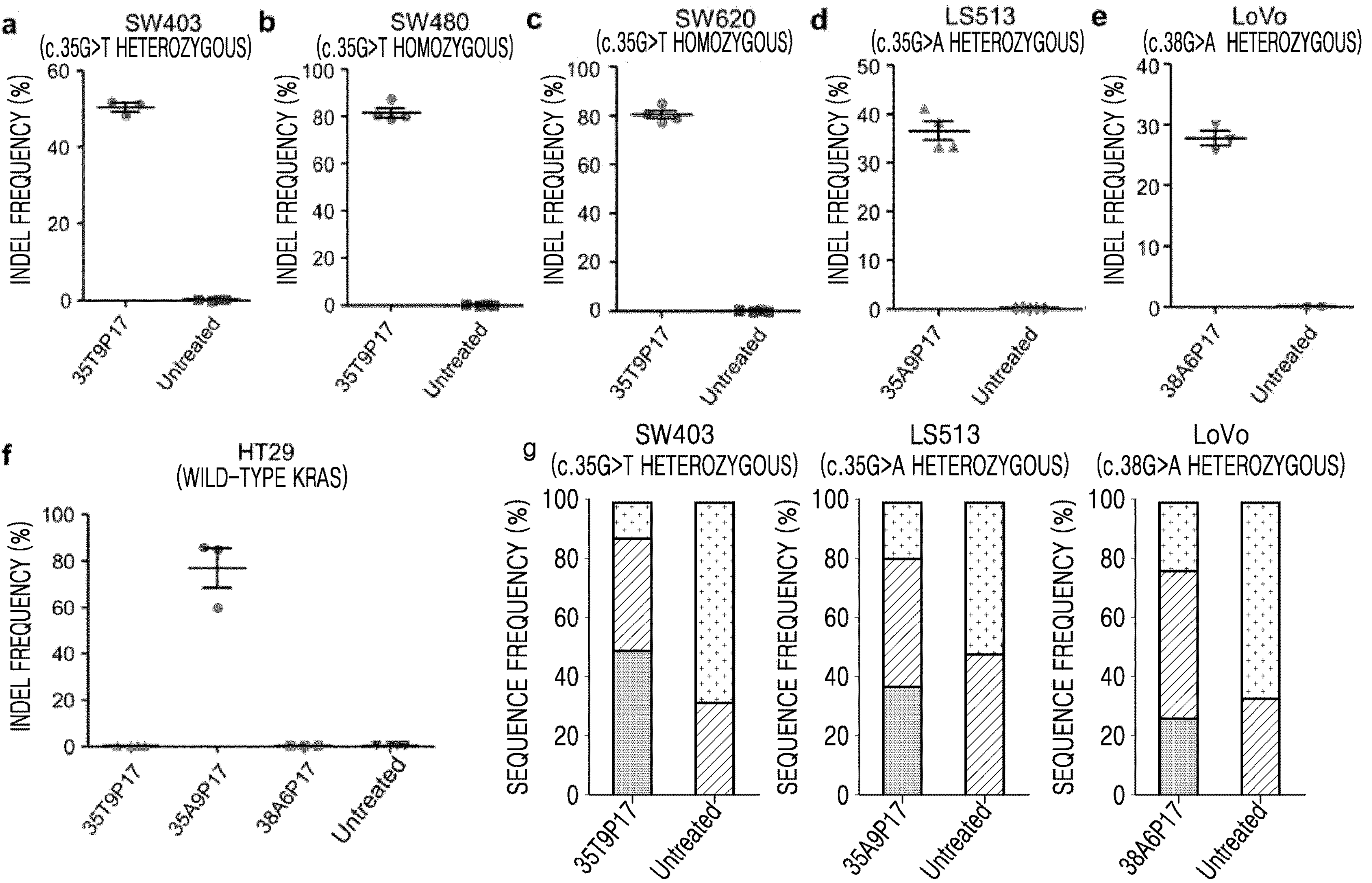
FIG. 3 is graphs showing results of deep sequencing of evaluating insertion/deletion frequencies at endogenous target KRAS sequences.

SW403 (heterozygous for c.35G>T mutation), SW480 (homozygous for c.35G>T mutation), SW620 (homozygous for c.35G>T mutation), LS513 (heterozyous for c.35G>A mutation), LoVo (heterozyous for c.38G>A mutation), and HT29 cell line (wild-type KRAS) were used as cancer cells. The insertion/deletion (indel) frequencies at the endogenous target KRAS sequences were evaluated by deep sequencing, and the results are shown in FIG. 3. In FIG. 3, A to F are graphs showing indel frequencies (error bars: standard mean error, "untreated": untreated with guide RNA), and G is a graph showing average sequence frequencies (▦; Indel, ▨: wild-type KRAS, "+": mutant KRAS).

As shown in FIG. 3, transduction of Cas9 and 35T9P17 guide RNA showed indel frequencies of 50% in SW403 cells and 81% and 80% in SW480 and SW620 cells, respectively. Further, transduction of Cas9 and 35A9P17 showed indel frequencies of 36% in LS51336, and transduction of Cas9 and 38A6P17 showed indel frequencies of 28% in LoVo. When these guide RNAs were transduced into HT29 cells, the indel frequencies were 02% for 35T9P17, 77% for 35A9P17, and 0.3% for 38A6P17 (FIG. 2F), indicating that 35A9P17 is highly selective for wild-type KRAS sequence, and 35T9P17 and 38A6P17 are highly selective for mutant KRAS sequence.

5. Effect of Removal of Mutant KRAS Sequence in Cancer Cells

It was examined whether removal of mutant KRAS sequence of cancer cells by using the selected guide RNAs affects cancer cell survival, proliferation, and tumorigenicity.

Cancer cells were transduced with Cas9-encoding lentiviral vectors (Addgene #52962), and then transduced with guide RNA-encoding vectors (Addgene #52961). As a negative control, a completely different sequence-targeting guide RNA without activity was used.

Figure 4A:
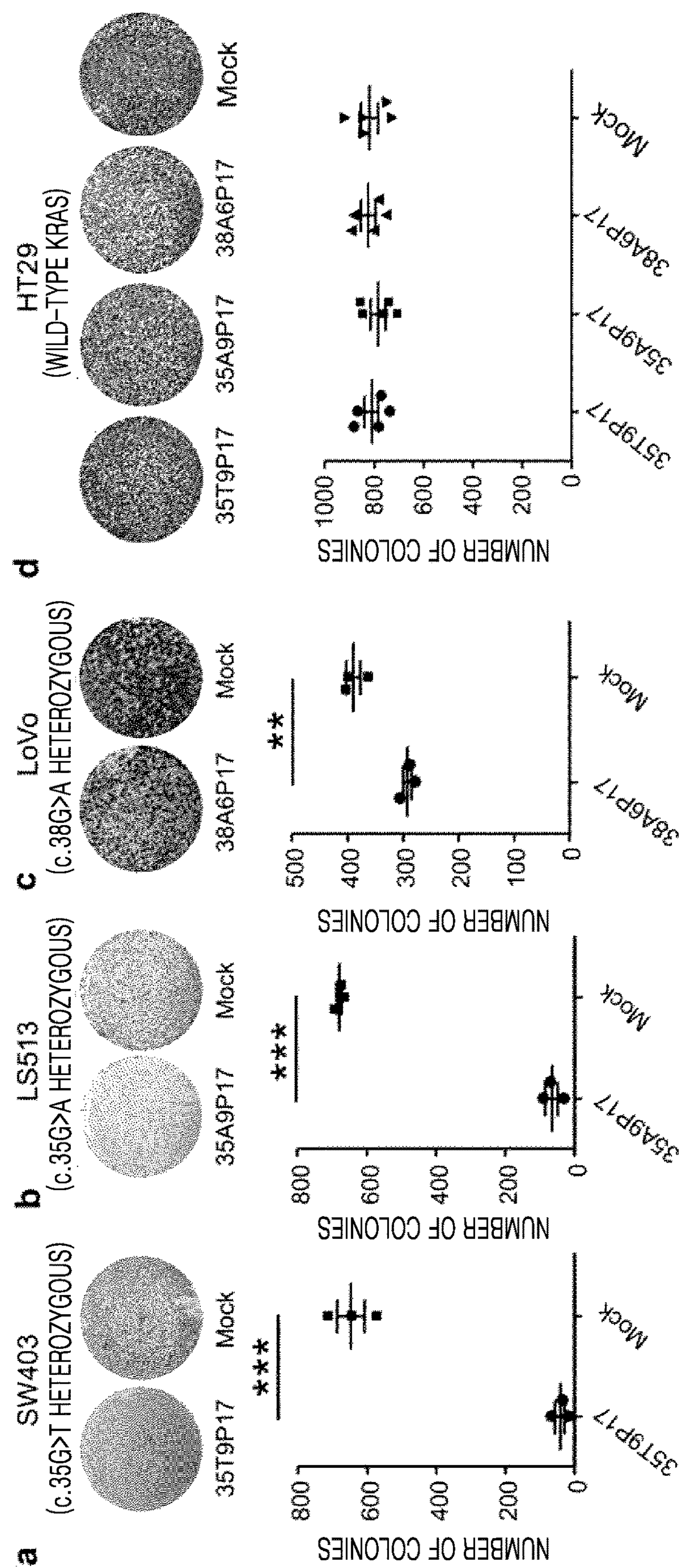
FIGS. 4A to 4C are images and graphs showing results of colony forming assay, soft agar assay, and MTS assay of cancer cells which were serially transduced with a Cas9-encoding lentiviral vector and a guide RNA-encoding vector.
Figure 4B:
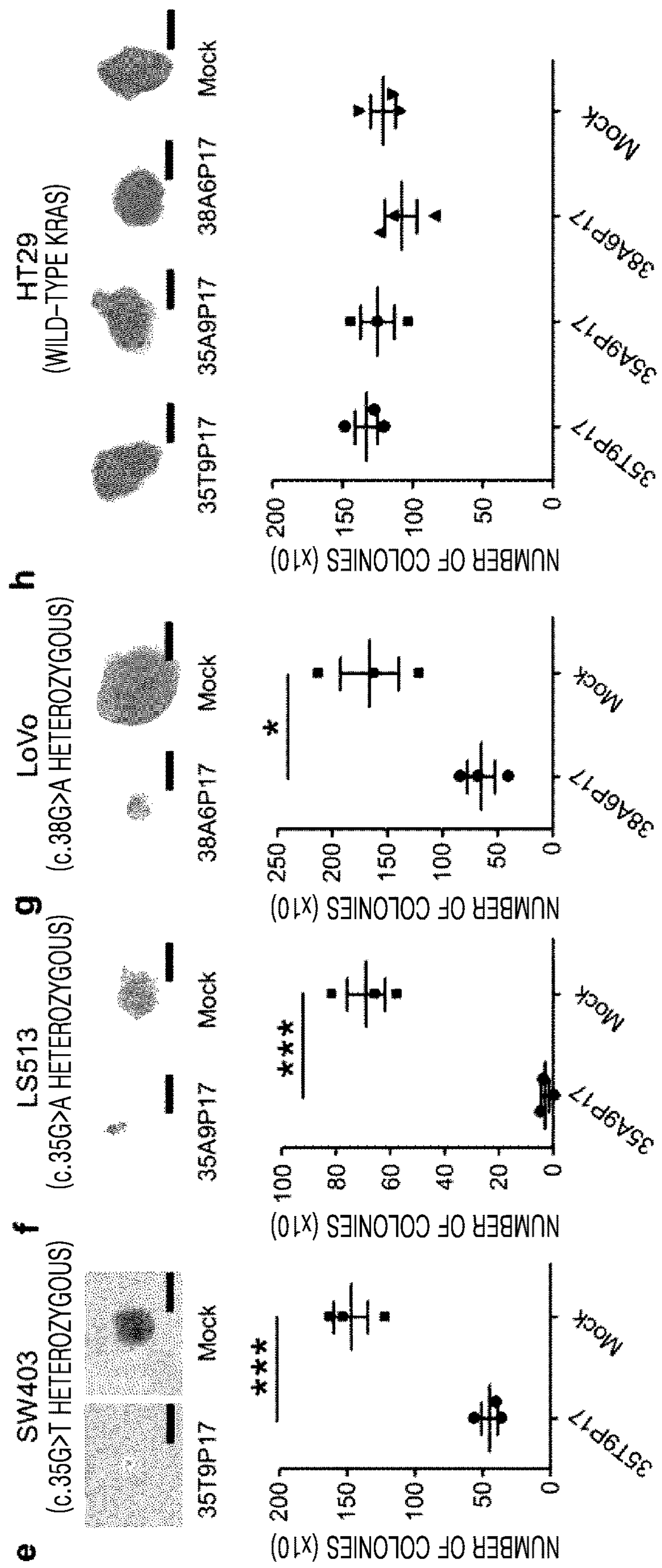
Figure 4C:
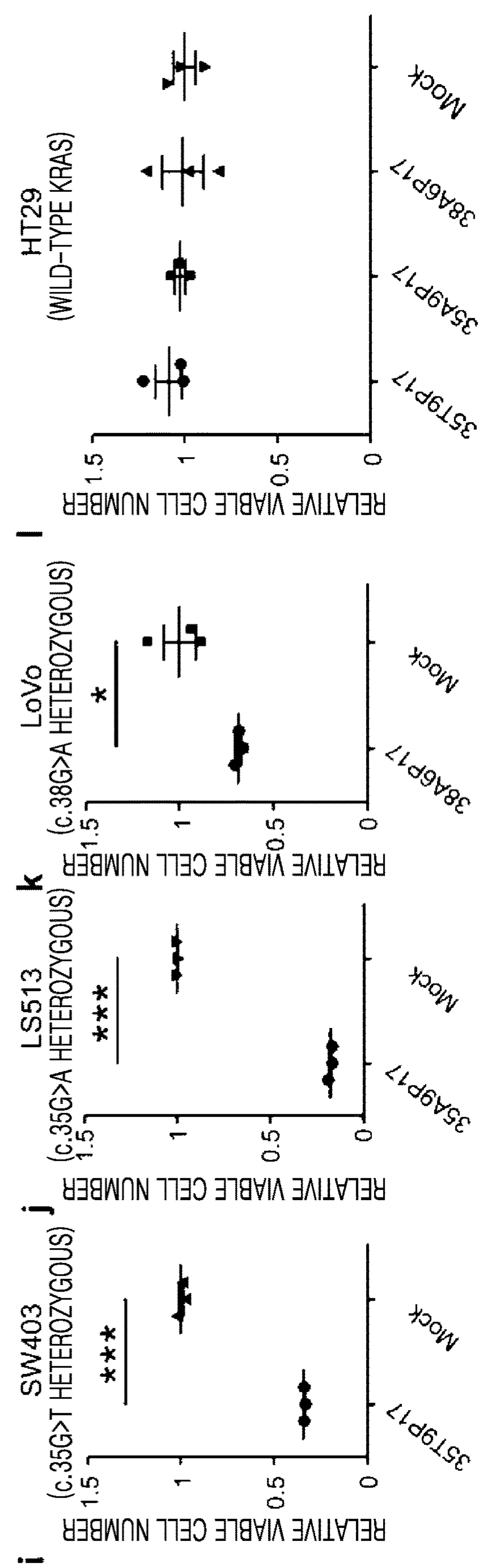

These transduced cells were subjected to colony forming assay, soft agar assay, and MTS assay, and the results are shown in FIGS. 4A to 4C, respectively (error bars: standard mean error, *: p<0.05, : p<0.01, *: p<0,001, “Mock”: negative control group).

Upper images A to D of FIG. 4A represent images of wells after 2% crystal violet staining, and upper images E to H of FIG. 4B represent formed colonies (scale bar=100 μm).

As shown in FIGS. 4A to 4D, expression of Cas9 and 35T9P17 guide RNA in SW403 cells led to 94% and 70% reductions in the number of colonies in colony forming assay and soft agar assay, respectively. Similar results were also observed in SW480 and SW620 cells. Furthermore, expression of Cas9 and 35A9P17 guide RNA in LS513 cells resulted in 91% and 96% reductions in the number of colonies in colony forming assay and soft agar assay, respectively. Meanwhile, the expression of Cas9 and 38A6P17 guide RNA in cancer cells reduced the number of colonies in colony forming assay and soft agar assay, but the reduction was only 25% and 61%, respectively, suggesting that 38A6P17 guide RNA partially inhibits the survival and tumorigenicity of KRAS mutant cancer cells, but 35T9P17 and 35A9P17 guide RNAs significantly inhibit the survival and tumorigenicity of cancer cells. When guide RNAs were expressed in a doxycycline-inducible manner, similar results were observed.

The effect of Cas9 and guide RNA on cell proliferation was evaluated by MTS cell proliferation assay. Cancer cells were transduced with Cas9 and guide RNA, and one day later, live cells were counted. 5000 cells per sample were plated into 96-well, and untransduced cells were removed using puromycin selection for 24 hours. After plating, an MTS reagent was added thereto, and cell proliferation was determined by incubation for 48 hours. The optical density at 490 nm of MTS reaction was measured and normalized to the optical density of the negative control. The relative number of cells transduced with guide RNA to cells transduced with the negative control guide RNA was determined, and the results are shown in FIG. 3C. As shown in FIG. 3C, the relative viable cell number in the population expressing Cas9 and 35T9P17 RNA were, on average, 0.34, 0.46, and 0.71 in SW403, SW480, and SW620 cells, respectively. Meanwhile, the expression of Cas9 and guide RNA in HT29 cells did not alter the number of cells in the MTS cell proliferation assay, suggesting that removal of mutant. KRAS with Cas9 and guide RNA inhibits proliferation or survival of cancer cells, but does not inhibit proliferation or survival of cells having the wild-type KRAS sequence.

6. Effect of Removal of Mutant KRAS Sequence In Vivo

It was examined whether the selected guide RNAs suppress tumor growth in vivo.

Figure 5A:
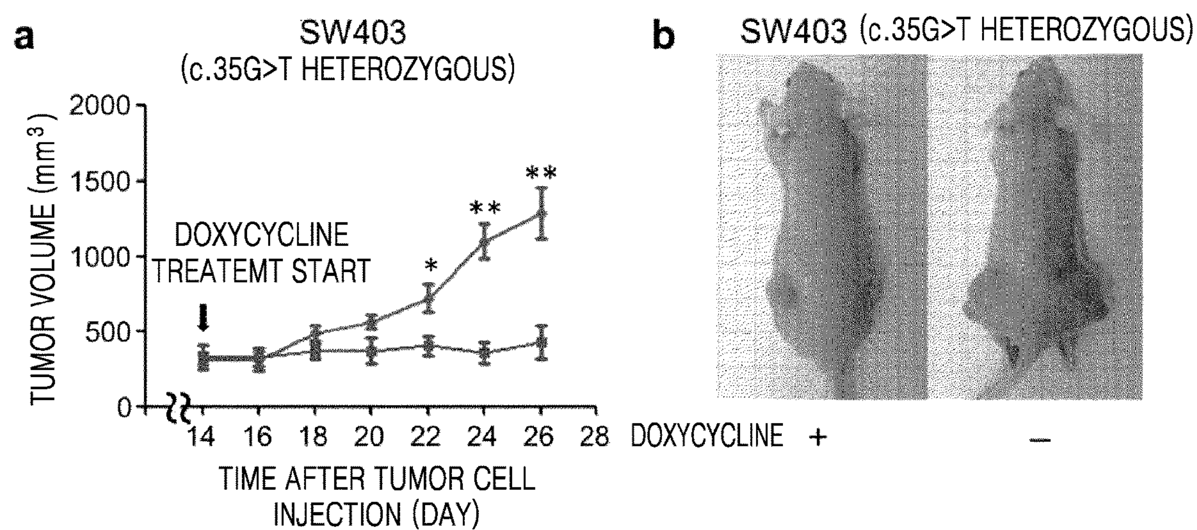
FIGS. 5A to 5C are images and graphs showing results of measuring tumor sizes and weights according to 35T9P17 guide RNA expression after transplanting nude mice with cancer cells which were serially transduced with a Cas9-encoding lentiviral vector and a guide RNA-encoding vector.
Figure 5B:
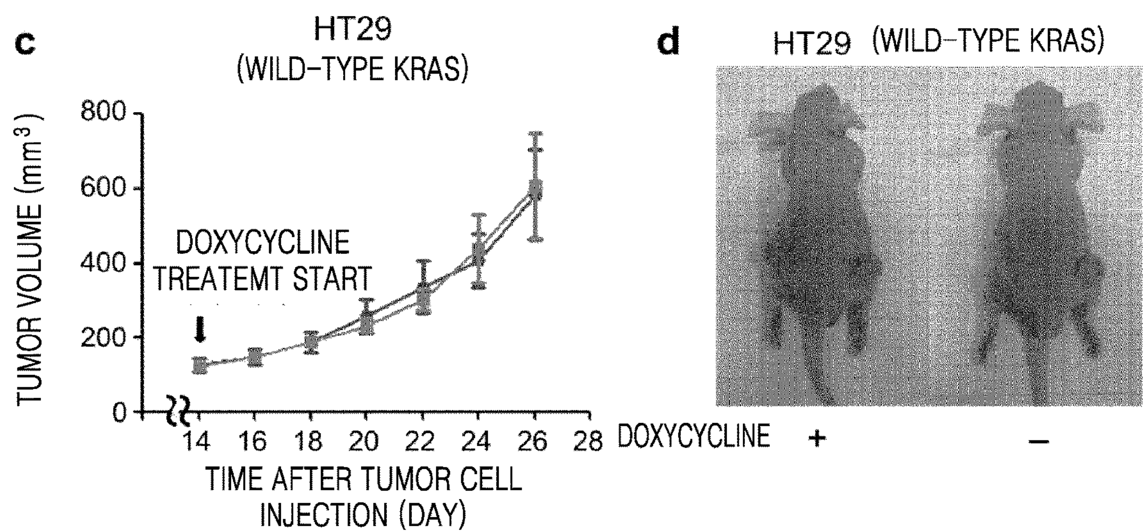
Figure 5C:
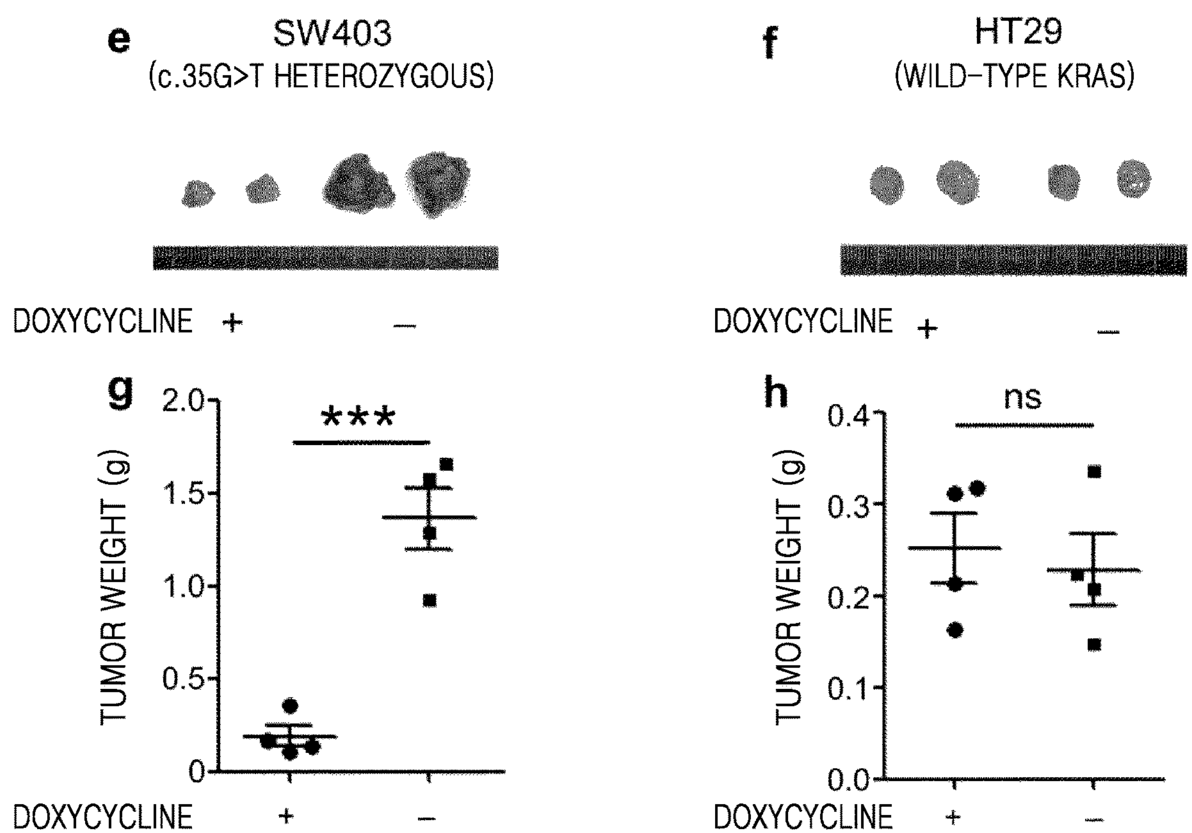

Cas9-expressing SW403 cells were transduced with a lentiviral vector. The cells were subsequently transduced with another lentiviral vector that expresses the 35T9P17 guide RNA in a doxycycline-inducible manner. Subcutaneous transplantation of these serially transduced cancer cells into nude mice led to tumor formation over 14 days. Then, doxycycline was administered to the mice to induce 35T9P17 guide RNA expression in the tumor cells. After transplantation of the cancer cells, tumor size and weight according to 35T9P17 guide RNA expression were measured and the results are shown in FIGS. 5A to 5C (in graphs of FIGS. 5A and 5B, ●: doxycycline untreated, ■: doxycycline treated, *: p<0.05, : p<0.01, *: p<0.001).

As shown in FIGS. 5A to 5C, 3519P17 guide RNA expression did not affect tumor sizes of mice injected with cells having the wild-type KRAS sequence, but significantly suppressed tumor growth and reduced tumor weights of mice injected with cells having the mutant KRAS sequence, suggesting that targeting mutant KRAS with CRISPR-Cas9 may control tumor growth in vivo.

7. Intra-Tumoral Delivery of Cas9 and Guide RNA Targeting Mutant KRAS (1) Use of Lentiviral Vector In Example 1.6, cancer cells transduced with Cas9 and 35T9P17 guide RNA were transplanted into nude mice to induce tumorigenesis, and anti-cancer effect was confirmed. Furthermore, it was confirmed whether external injection of Cas9 and 35T9P17 guide RNA into tumor cells also exhibits the anti-cancer effect.

5-week-old athymic male BALB/c nude mice were prepared. $2\times10^6$ of SW403 cancer cells having KRAS c.35G>T mutant were subcutaneously injected into the flanks of the prepared nude mice (six mice per group) and allowed to form tumors over 2 weeks, Meanwhile, as a control group, HT29 cell line containing the wild-type KRAS were subcutaneously injected into athymic mice.

To deliver Cas9 and 35T9P17 guide RNA to cancer cells, each tumor of the mice was directly injected with lentivirus expressing Cas9 and 35T9P17 guide RNA ($1\times10^8$ TU lentivirus in 50 μl PBS) with insulin syringes (BD Biosciences, 31 gauge) three times with 3 day-intervals between injections. As a negative control group, each tumor of the mice was injected with lentivirus expressing only Cas9. Thereafter, tumor size was evaluated every 3 days using a caliper. Mice were sacrificed 5 weeks after the tumor cell injection, and the tumors were removed from the mice.

Figure 6:
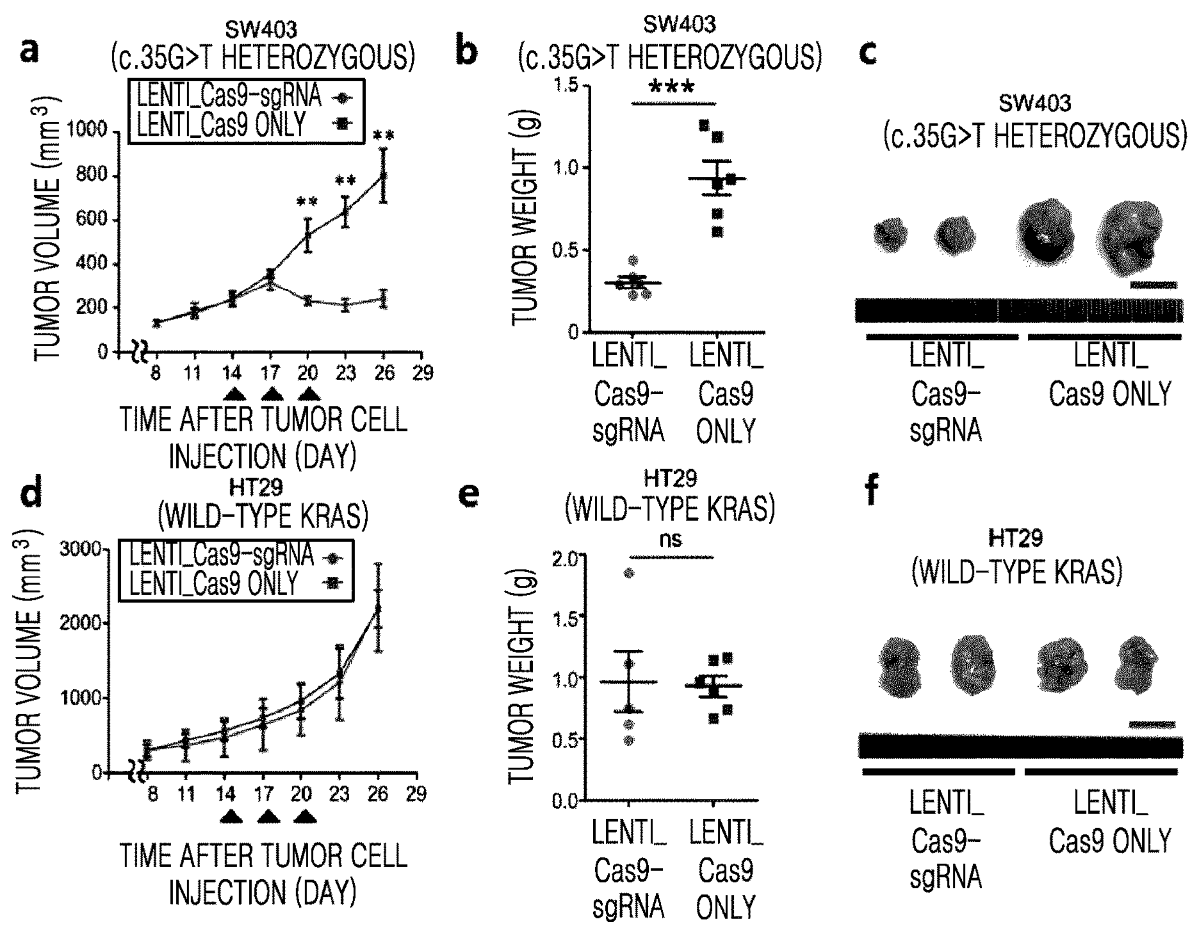
FIG. 6 shows graphs of tumor volumes ($mm^3$) and weights (g) and images of tumors according to 35T9P17 guide RNA expression after transplanting nude mice with cancer cells or a common cell line followed by intra-tumoral injection of a Cas9-encoding lentiviral vector and a guide RNA-encoding vector.

Volumes ($mm^3$), weights (g), and images of the removed tumor tissues are shown in FIG. 6 (A to C: transplantation of SW403 cancer cells, D to F: transplantation of HT29 cell line, error bars: standard error of the measurement, sgRNA: 3519P17 guide RNA, triangle: lentivirus injection, ***: p<0.001, ns: not significant, scale bars in C and F. 1 cm).

As shown in FIG. 6, intra-tumoral injection of lentivirus expressing Cas9 and 35T9P17 guide RNA inhibited the tumor growth, whereas the negative control group showed the robust tumor growth. Delivery of Cas9 and 35T9P17 guide RNA into tumors which were generated using cancer cells without mutant KRAS did not affect tumor growth, which was comparable to those injected with lentivirus expressing only Cas9.

Accordingly, it was confirmed that 35T9P17 guide RNA has the specificity for cancer cells containing the KRAS c.35G>T mutation, and intra-tumoral injection of the molecular scissors using the lentiviral vector also exhibits the anti-cancer effect.

(2) Use of Adeno-Associated Viral Vector

To examine whether use of an adeno-associated viral (AAV) vector exhibits the similar effect to use of the lentiviral vector, 35T9P17 guide RNA was cloned into a PX552 vector (Addgene #60958). A miniCMV-Cas9-shortPolyA plasmid (provided by Dr. Dirk Grimm, Heidelberg University Hospital, Germany) was used for Cas9 delivery.

35T9P17 guide RNA-containing AAV vector and miniCMV-Cas9-shortPolyA plasmid were co-transfected into HEK293T cells, together with pAAV-RC2 (Cell Biolabs, VPK-402) and helper DNA (Cell Biolabs, VPK-402), and then cultured for about 48 hours to obtain a virus-containing supernatant. The obtained AAV vector ($1\times10^{12}$ gc/ml AAV in 50 μl of PBS) was injected into tumors of athymic nude mice, in the same manner as in lentivirus. As a negative control group, an AAV vector encoding only green fluorescent protein (GFP) was used. Tumor size was evaluated every 2 days using a caliper. Mice were sacrificed 12 days after AAV injection, and the tumor tissues were removed from the mice.

Figure 7:
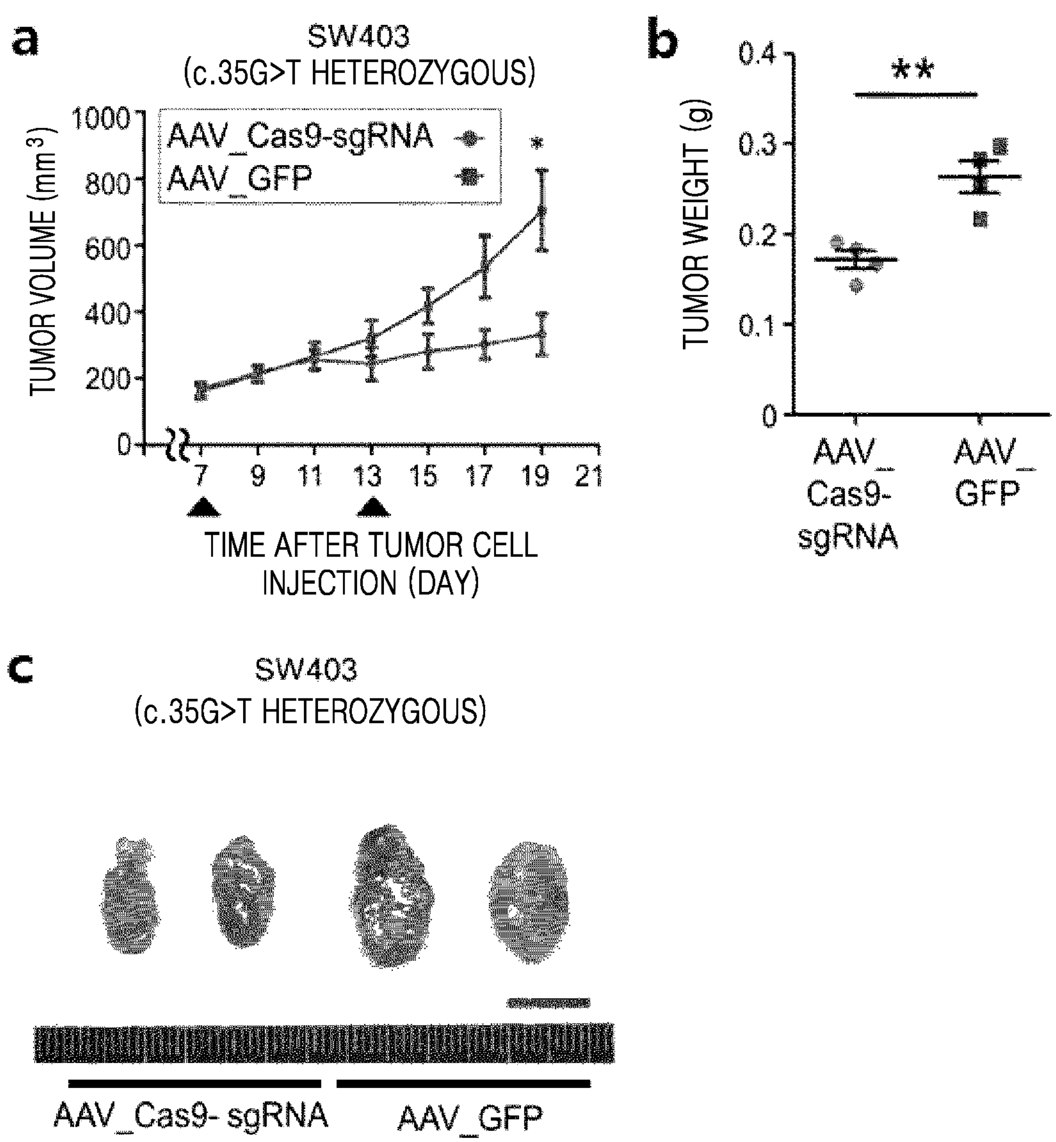
FIG. 7 shows graphs of tumor volumes ($mm^3$) and weights (g) and images of tumors according to 35T9P17 guide RNA expression after transplanting nude mice with cancer cells or a common cell line followed by intra-tumoral injection of a Cas9-encoding AAV vector and a guide RNA-encoding vector.

Volumes ($mm^3$), weights (g), and images of the removed tumor tissues are shown in FIG. 7 (A to C: transplantation of SW403 cancer cells, error bars: standard error of the measurement, sgRNA: 35T9P17 guide RNA, triangle: AAV injection, **: $p<0.01$, *: $p<0.1$, scale bar in C: 1 cm).

As shown in FIG. 7, use of AAV also resulted in significant control of tumor growth, albeit to a lesser extent than caused by use of lentivirus.

Accordingly, it was confirmed that, regardless of the type of viral vector, intra-tumoral injection of the molecular scissors exhibits the anti-cancer effect.

The invention claimed is:

1. A guide RNA specifically recognizing a mutant KRAS sequence, the guide RNA comprising:

a CRISPR RNA (crRNA), and a trans-activating crRNA (tracrRNA), wherein the crRNA is specific to a target nucleotide sequence, wherein the tracrRNA is capable of interacting with a Cas polypeptide, wherein the mutant KRAS sequence comprises a polynucleotide selected from the group consisting of:

5'-CTTGTGGTAGTTGGAGCTGTTGGCGTAGGCAAGAGTGCC-3' (SEQ ID NO: 87);

5'-CTTGTGGTAGTTGGAGCTGATGGCGTAGGCAAGAGTGCC-3' (SEQ ID NO: 88);

5'-CTTGTGGTAGTTGGAGCTGGTGACGTAGGCAAGAGTGCC-3' (SEQ ID NO: 89);

5'-CTTGTGGTAGTTGGAGCTTGTGGCGTAGG-3' (SEQ ID NO: 90);

5'-CTTGTGGTAGTTGGAGCTCGTGGCGTAGG-3' (SEQ ID NO: 91); and

5'-CTTGTGGTAGTTGGAGCTGCTGGCGTAGGCAAGAGTGCC-3' (SEQ ID NO: 92), and wherein the target nucleotide sequence comprises a protospacer adjacent motif (PAM) which is recognized by the Cas polypeptide, wherein the guide RNA comprises a nucleotide sequence identical or complementary to two or more consecutive polynucleotides in a nucleotide sequence selected from the group consisting of SEQ ID NOS: 42 to 84.

2. The guide RNA of claim 1, wherein the PAM comprises a nucleotide sequence selected from the group consisting of 5'-TGG-3', 5'-TAG-3', 5'-AGG-3', and 5'-CTG-3'.

3. The guide RNA of claim 1, wherein the guide RNA has a length of 10 nucleotides to 30 nucleotides.

4. A composition for mutating a nucleotide sequence encoding a mutant KRAS polypeptide in the genome of a cell, the composition comprising the guide RNA of claim 1 and a Cas polypeptide, wherein the sequence of the mutant KRAS comprises a polynucleotide selected from the group consisting of:

5'-CTTGTGGTAGTTG-GAGCTGTTGGCGTAGGCAAGAGTGCC-3' (SEQ ID NO: 87;

5'-CTTGTGGTAGTTGGAGCT-GATGGCGTAGGCAAGAGTGCC-3' (SEQ ID NO: 88);

5'-CTTGTGGTAGTTG-GAGCTGGTGACGTAGGCAAGAGTGCC-3' (SEQ ID NO: 89);

5'-CTTGTGGTAGTTGGAGCTTGTGGCGTAGG-3' (SEQ ID NO: 90);

5'-CTTGTGGTAGTTGGAGCTCGTGGCGTAGG-3' (SEQ ID NO: 91); and

5'-CTTGTGGTAGTTG-GAGCTGCTGGCGTAGGCAAGAGTGCC-3' (SEQ ID NO: 92).

5. The composition of claim 4, wherein the composition is for in vitro or in vivo administration.

6. The composition of claim 4, the Cas polypeptide is comprised in the form of a second polynucleotide comprising a nucleotide sequence encoding the Cas polypeptide.

7. The composition of claim 4, wherein the Cas polypeptide is a Cas9 polypeptide or a Cpf1 polypeptide.

8. A pharmaceutical composition for preventing or treating a cancer, the composition comprising the composition of claim 4, wherein the cancer is the KRAS gene mutant cancer.

9. The pharmaceutical composition of claim 8, wherein the cancer is selected from the group consisting of pancreatic cancer, colon cancer, lung cancer, breast cancer, skin cancer, head and neck cancer, colorectal cancer, stomach cancer, ovarian cancer, prostate cancer, bladder cancer, urethral cancer, liver cancer, kidney cancer, clear cell sarcoma, melanoma, cerebrospinal tumor, brain cancer, thymoma, mesothelioma, esophageal cancer, biliary cancer, testicular cancer, germ cell tumor, thyroid cancer, parathyroid cancer, cervical cancer, endometrial cancer, lymphoma, myelodysplastic syndromes (MDS), myelofibrosis, acute leukemia, chronic leukemia, multiple myeloma, Hodgkin's disease, neuroendocrine tumor, and sarcoma.

10. A method of mutating a nucleotide sequence encoding a mutant KRAS polypeptide in the genome of a cell, the method comprising incubating the cell with the composition of claim 4.

11. A method of preventing or treating a cancer, the method comprising administering to a subject the composition of claim 4.

12. The method of claim 11, wherein the subject has a genome comprising a nucleotide sequence encoding a mutant KRAS polypeptide.

13. The guide RNA of claim 1, wherein the guide RNA is a single-chain guide RNA (sgRNA).

14. The composition of claim 4, wherein each of the guide RNA and the Cas polypeptide is comprised in a vector.

15. The composition of claim 14, wherein the vector is a plasmid or a viral vector.

* * * * *